United States Patent
Gao

(10) Patent No.: US 11,610,643 B2
(45) Date of Patent: Mar. 21, 2023

(54) GMDAI PERSONALIZED HEALTH FORMULA SYSTEM AND COMPUTER STORAGE MEDIUM COMPRISING THE SAME

(71) Applicant: Govita Tech Limited, Hong Kong (HK)

(72) Inventor: Vincent Chun Xin Gao, Hong Kong (HK)

(73) Assignee: Govita Tech Limited, Hong Kong (HK)

( * ) Notice: Subject to any disclaimer, the term of this patent is extended or adjusted under 35 U.S.C. 154(b) by 125 days.

(21) Appl. No.: 17/330,439

(22) Filed: May 26, 2021

(65) Prior Publication Data

US 2022/0328126 A1  Oct. 13, 2022

(30) Foreign Application Priority Data

Apr. 7, 2021  (CN) .......................... 202110373885.X

(51) Int. Cl.

| | | |
|---|---|---|
| G16B 5/00 | (2019.01) | |
| G16B 20/20 | (2019.01) | |
| G16H 10/40 | (2018.01) | |
| G16H 50/20 | (2018.01) | |
| G16H 10/60 | (2018.01) | |
| G16H 50/30 | (2018.01) | |
| G16B 20/00 | (2019.01) | |
| G16H 20/60 | (2018.01) | |
| G16B 40/00 | (2019.01) | |

(52) U.S. Cl.
CPC ............... *G16B 5/00* (2019.02); *G16B 20/00* (2019.02); *G16B 20/20* (2019.02); *G16B 40/00* (2019.02); *G16H 10/40* (2018.01); *G16H 10/60* (2018.01); *G16H 20/60* (2018.01); *G16H 50/20* (2018.01); *G16H 50/30* (2018.01)

(58) Field of Classification Search
None
See application file for complete search history.

(56) References Cited

U.S. PATENT DOCUMENTS

| 9,011,153 B2 * | 4/2015 | Bennett ................. G16H 20/30 434/127 |
| 2011/0010099 A1 * | 1/2011 | Adourian ................. G16B 5/30 702/19 |
| 2014/0310019 A1 * | 10/2014 | Blander ................. G16H 40/67 705/2 |

* cited by examiner

*Primary Examiner* — Lori A. Clow

(57) ABSTRACT

A personalized health formula system which combines genetic and metabolic data to generate personalized intervention plan, termed Genetic and Metabolic Data Associated Intervention (GMDAI), as well as a computer readable medium and device containing the same is disclosed. The GMDAI personalized health formula system includes a pathway decision module and a supplement intervention module. The pathway decision module can make a decision of increasing or decreasing one or more of the markers by weighing detected levels of these markers, and the supplement intervention module can recommend a personalized supplementation formula including the type and dosage of supplement.

2 Claims, 12 Drawing Sheets

GMDAI PERSONALIZED HEALTH FORMULA SYSTEM AND COMPUTER STORAGE MEDIUM COMPRISING THE SAME

CROSS-REFERENCE TO RELATED APPLICATIONS

The present application claims the benefit of Chinese Patent Application No. 202110373885.X filed on Apr. 7, 2021, the contents of which are hereby incorporated by reference.

TECHNICAL FIELD

The present invention relates to the art of biomedicine, in particular to a personalized health formula system related to Genetic and Metabolic Data Associated Intervention (GMDAI) with personalized supplements, as well as a computer readable medium and device comprising the same.

BACKGROUND

Human health and lifespan are influenced by our genes as well as our diet, lifestyle and other environmental factors. Biological pathways are series of actions among molecules in a cell that lead to a certain product or a change in the cell to support the normal operation of our lives. There are three major biological pathways (metabolic, gene-regulation, and signal transduction) in human cells to support our lives. In the gene-regulation pathway, our genes encode metabolic enzymes, receptors, and transporters that are active in the metabolic biosynthesis and signal transduction pathways. By the identification of selected genetic polymorphisms, and parallel testing of key metabolite levels in these biochemical pathways, we can provide much better understanding of personal health status. This detailed understanding enables us to predict a predisposition to certain disease risks at a cellular level, and provide a personalized intervention plan which details types of heath supplements with optimal dosages and other lifestyle change recommendations. The aim of this personalized intervention plan is to improve and maintain our clients' health and help them to delay the effects of aging.

Oxidative metabolism in living organisms produces free radicals, which also participate in cellular signal transduction. The in vivo antioxidant system is necessary for maintaining the metabolic balance of free radicals. However, dysregulation of this system can induce the in vivo accumulation of free radicals. When the cellular antioxidant protection mechanisms are not sufficient, reactive oxygen species accumulate and become toxic to the cells; this state is called oxidative stress. Humans have a complete defense system to eliminate reactive oxygen species (ROS), including enzymatic and non-enzymatic mechanisms. The enzymatic defense system includes superoxide dismutase (SOD), catalase (CAT) and glutathione peroxidase (GPX) in the trans-sulfuration pathway. SOD catalyze dismutation of superoxide radicals $O_2^-$ to $H_2O_2$. CAT catalyzes the decomposition of $H_2O_2$ into $H_2O$ and $O_2$. GPX uses glutathione (GSH) to reduce hydroperoxides to $H_2O$ or alcohol compounds. The non-enzymatic mechanism mainly includes some low molecular weight antioxidant molecules, such as α-tocopherol, vitamin C and GSH.

GSH, namely γ-L-glutamyl-L-cysteinyl-glycine, is a biologically active non-protein thiol compound that exists widely in living organisms. Under physiological conditions, glutathione exists mainly in two forms, reduced glutathione (GSH) and oxidized glutathione (GSSG), wherein the active reduced GSH accounts for about 90% of total of both forms. GSSG can be reduced to GSH by glutathione reductase (GR) while NADPH is consumed at the same time. GSH has a free sulfhydryl group and a strong ability to donate electrons or proton hydrogen. It can be used as a hydrophilic antioxidant and a cofactor for antioxidant enzymes, and fulfills two fundamental physiological functions in living organisms: (a) protection of DNA, proteins and other biological molecules against oxidative damage as the most abundant intracellular antioxidant; (b) detoxification of exogenous substances by glutathione-S-transferase (GST). Therefore, increasing the content or ratio of reduced GSH in the body is beneficial for decreasing the oxidative damage of cells and promotion of cellular detoxification.

In addition, GSH has anti-convulsant, anti-thrombotic and anti-atherosclerotic effects. Scientific research has shown that when there are lesions in tissues, the levels of glutathione and the ratio of GSH to GSSG in tissues will change, but whether they increase or decrease in the short term varies depending on the disease. Maintaining a dynamic balance of the high ratio of GSH to GSSG is of a great importance for our health, especially as high levels of GSH bind to NMDA receptors through biological signal transduction pathways and regulate brain neurotransmitters to maintain brain health. Moreover, GSH-related pathways involve a considerable number of interrelated enzymes with intricate interactions. Manual evaluation of the GSH-related biomarkers would be prone to high level of bias and would be highly time-consuming and costly. Hence, there is an urgent need for a system with rapid and unbiased evaluation of genetic and metabolic markers in the trans-sulfuration biological pathways, which can also produce personalized health formula to recommend appropriate types and dosages of supplements. This personalized intervention supports the dynamic balance of biological system in the trans-sulfuration biological pathways which is necessary for adequate response to oxidative stress, optimal functioning of the immune system and effective cellular detoxification; all these processes in return underpin our health and wellbeing, and contribute to the delay of aging.

CONTENT OF THE PRESENT INVENTION

In order to solve the technical problem of lacking a rapid and unbiased evaluation of the status of biological pathways, specifically evaluation of trans-sulfuration pathway based on the combined evaluation of genetic and metabolic markers, which could be used to generate personalized health formula system in the prior art, a GMDAI personalized health formula system and computer storage medium comprising the same are provided.

In order to solve the technical problems described above, the first technical solution of the present invention is a computer-assisted personalized health formula system which relates to Genetic and Metabolic Data Associated Intervention (GMDAI) with supplements comprising of:

(1) a pathway decision module: the pathway decision module determines relevant markers in biological pathways using biological pathway omics (BPO), where the biological pathways comprise gene-regulation pathways, metabolic pathways and signal transduction pathways, and the markers comprise genetic, metabolic and signal transduction markers; wherein, a physiological level of the markers (e.g. concentration of the metabolic marker) is obtained first and then assigned into one or more of High, Increased, Normal, Decreased or Low categories; and then a decision of increasing or decreasing one or more of the markers is made by weighing the detected levels of all evaluated markers;

(2) a supplement intervention module: the supplement intervention module recommends a personalized supplementation formula based on the BPO and the decision provided by the pathway decision module; the supplementation formula consists of one or more supplements, which regulate activity of genetic markers, affect the detected levels of the metabolic markers and/or signal transduction markers; the form and dose of the supplements is determined according to the combined evaluation provided by both above-described modules.

In the present invention, the term "supplement" refers to nutritional supplements, or health supplements.

Preferably, the GMDAI personalized health formula system further comprises:

(3) a formula finalization module: the formula finalization module optimizes the supplementation formula, which comprises the following steps:

(i) removing duplicate supplements; and/or, (ii) selecting a lower dose if there is a conflict in the dosage of the supplements.

In some preferred embodiments, in the pathway decision module, the activity of the genetic markers is assigned into High, Increased, Normal, Decreased or Low according to the genotype of their SNP; and/or, when the detected levels of the metabolic markers are below a preset percentile cutoff, between lower and upper percentile cutoff or higher than upper percentile cutoff; the values of the metabolic markers are respectively determined as low, normal and high.

Preferably, the High, Increased, Normal, Decreased or Low of the activity of a genetic marker is assigned as 2, 1, 0, −1 and −2 respectively; and when more than one marker of a gene are detected, the activity of the gene is the average value of more than one of the markers.

In some preferred embodiments, in the pathway decision module, the percentile is calculated by the following equation:

$$n^{th} \text{percentile} = \text{AVG} + \text{SD} * (z \text{ score of } n^{th} \text{percentile})$$

wherein, n is any value between 0 and 100, AVG represents average value of samples, SD represents standard deviation, and z is a probability value of the percentile in the standard normal distribution model; thus, the detected level of the metabolite in the individual sample can be determined as low, normal or high based on the percentile and concentration of the marker.

In some preferred embodiments, in the pathway decision module, the genetic markers of the gene-regulation pathways comprise GLS2, GCLC, GCLM, GSS, GSR, GSTP1, GSTM1, GSTT1, GPX1, GPX4, SEPP1, SOD 1, SOD2, SOD3, CAT and GGT1; the metabolic markers of the metabolic pathways comprise GSH, GSSG and GSH:GSSG ratio;

and/or, in the supplement intervention module, the supplements that affect the detected levels of metabolic markers comprise glutathione (GSH) and N-Acetyl Cysteine (NAC), and the supplements that regulate the activity of genetic markers comprise isothiocyanate (ITC), alpha-lipoic acid (ALA), vitamin C (VC), vitamin E (VE), nicotinamide adenine dinucleotide (NAD+), vitamin B2, selenium (Se), ubiquinol (Q10H2), zinc (Zn), copper (Cu) and manganese (Mn).

Preferably, in the pathway decision module, the activity of the genetic markers is determined based on the genotype corresponding to the SNPs of each gene as shown in the following table;

| Gene | SNP or mutation | Genotype | Enzyme Activity |
|---|---|---|---|
| GLS2 | rs2657879 | AA | Decreased |
| | | AG | Normal |
| | | GG | Increased |
| GCLC | rs761142 | AA | Normal |
| | | AC | Decreased |
| | | CC | Low |
| GCLM | rs41303970 | GG | Normal |
| | | GA | Decreased |
| | | AA | Low |
| GSS | rs3761144 | GG | Normal |
| | | GC | Decreased |
| | | CC | Low |
| GSR | rs1002149 | GG | Normal |
| | | GT | Increased |
| | | TT | High |
| GSTP1 | rs1695 | GG | Low |
| | | AG | Decreased |
| | | AA | Normal |
| GSTM1 | Null mutation | Present | Normal |
| | | Null mutation | Low |
| GSTT1 | Null mutation | Present | Normal |
| | | Null mutation | Low |
| GPX1 | rs1050450 | GG | Normal |
| | | AG | Low |
| | | AA | Low |
| GPX4 | rs713041 | TT | Decreased |
| | | CT | Normal |
| | | CC | Normal |
| SEPP1 | rs7579 | CC | Normal |
| | | CT | Increased |
| | | TT | Increased |
| SOD1 | rs10432782 | TT | Normal |
| | | GT | Increased |
| | | GG | High |
| SOD1 | rs1041740 | CC | Normal |
| | | CT | Decreased |
| | | TT | Low |
| SOD2 | rs4880 | AA | High |
| | | AG | Increased |
| | | GG | Normal |
| SOD3 | rs2536512 | GG | Normal |
| | | AG | Decreased |
| | | AA | Low |
| CAT | rs769217 | CC | Normal |
| | | CT | Decreased |
| | | TT | Low |
| GGT1 | rs4820599 | AA | Normal |
| | | AG | Increased |
| | | GG | High; | and/or, in the detected levels of the metabolic markers, the lower percentile cutoff of GSH is the $60^{th}$ percentile, and the upper percentile cutoff is the $90^{th}$ percentile; the lower percentile cutoff of the GSSG is the $10^{th}$ percentile, and the upper percentile cutoff is the $90^{th}$ percentile; and the lower percentile cutoff of the GSH:GSSG is the $60^{th}$ percentile, and the upper percentile cutoff is the $90^{th}$ percentile.

In some preferred embodiments, in the pathway decision module, the following assessments and decisions are made at the same time:

(A) when GSH level is high, the decision is to decrease GSSG level;

(B) when GSH level is low:

(a) when GSSG level is low, the decision is to increase GSH level;

(b) when GSSG level is normal or high, the decision is to increase GSH level and decrease GSSG level at the same time;

(C) when GSH:GSSG is low:
(a) when GSH level is high, the decision is to decrease GSSG level;
(b) when GSH level is normal or low:
(i) when GSSG level is normal or high, the decision is to increase GSH level and decrease GSSG level;
(ii) when GSSG level is low, the decision is to increase GSH level.

In the present invention, (A), (B), and (C) are only used to distinguish different evaluations and decisions, and there is no actual order, so are symbols (a), (b) and (i), (ii).

Preferably, in the supplement intervention module,
(A) when the decision is to increase level of GSH, then the selection of NAC or GSH depends on activity of the following four genes: GSS, GCLC, GCLM, and GLS2:
(a) if the lowest activity of the four genes is higher than Decreased, then NAC is selected as a supplement;
(b) if the lowest activity of the four genes is lower than Decreased, then GSH is selected as a supplement;
(B) when the decision is to decrease GSSG level, then B2 and NADPH are selected as supplements.

More preferably, in the supplement intervention module,
(A) the dose of NAC is determined by the activities of GSTM1, GSTP1, GSTT1, GSR, GSS, GCLC, GCLM and GLS2; and/or,
(B) the dose of GSH is determined by the activities of GSTM1, GSTP1, GSTT1 and GSR; and/or,
(C) the doses of B2 and NADPH are determined by the activity of GSR.

More preferably, in the supplement intervention module, when the decision is to increase GSH level, it also comprises use of ITC and Q10H2 as supplements, and/or use of selenium, zinc, copper and manganese as supplements.

In some preferred embodiments, in the supplement intervention module,
when the decision is to increase GSH level,
switch to the first sub-module to evaluate the minimum activity among the activities of GSS, GCLC, GCLM or GLS2:
(A) when the minimum activity is Normal or Decreased, NAC is used as a supplement; then, average activity of GSTM1, GSTP1, GSTT1, GSR, GSSS, GCLC, GCLM or GLS2 is determined:
when the average activity is Decreased, a medium dose of NAC is used as a supplement;
when the average activity is Low, a high dose of NAC is used as a supplement;
when the average activity is Normal, Increased or High, a low dose of NAC is used as a supplement;
(B) when the minimum activity is Increased or High, GSH is used as a supplement; then, average activity of GSTM1, GSTP1, GSTT1 or GSR is determined:
when the average activity is Decreased, a medium dose of GSH is used as a supplement;
when the average activity is Low, a high dose of GSH is used as a supplement;
when the average activity is Normal, Increased or High, a low dose of GSH is used as a supplement; and/or,
switch to the second sub-module to evaluate activity of GGT1:
when the activity is Increased, a medium dose of Q10H2 is used as a supplement;
when the activity is High, a high dose of Q10H2 is used as a supplement;
when the activity is Normal, Decreased or Low, a low dose of Q10H2 is used as a supplement; and/or, switch to the third sub-module to evaluate average activity of GSTM1, GSTP1, GSTT1 or GCLC:
when the activity is Decreased, a medium dose of isothiocyanate is used as a supplement;
when the activity is Low, a high dose of isothiocyanate is used as a supplement;
when the activity is Normal, Increased or High, a low dose of isothiocyanate is used as a supplement; and/or,
switch to the fourth sub-module to evaluate average activity of GPX1, GPX4 or SEPP 1:
when the activity is Decreased, a medium dose of selenium and alpha-lipoic acid is used as a supplement;
when the activity is Low, a high dose of selenium and alpha-lipoic acid is used as a supplement;
when the activity is Normal, Increased or High, or high, a low dose of selenium and alpha-lipoic acid is used as a supplement; and/or,
switch to the fifth sub-module to evaluate average activity of SOD1 or SOD3:
when the activity is Decreased, a medium dose of zinc, vitamin E and copper is used as supplements;
when the activity is Low, a high dose of zinc, vitamin E (if GSTP1 has low activity, otherwise, a low dose vitamin E is given) and copper is used as supplements;
when the activity is Normal, Increased or High, a low dose of zinc, vitamin E and copper is used as supplements; and/or,
switch to the sixth sub-module to evaluate activity of SOD2:
when the activity is Decreased, a medium dose of manganese and vitamin C is used as a supplement;
when the activity is Low, a high dose of manganese and vitamin C is used as a supplement;
when the activity is Normal, Increased or High, a low dose manganese and vitamin C is used as a supplement; and/or,
when the decision is to decrease GSSG level, switch to the seventh sub-module to evaluate GSR activity:
when the GSR activity is Normal, a medium dose of B2 and/or NAD+ is used;
when the GSR activity is Increased or High, a low dose of B2 and/or NAD+ is used;
when the GSR activity is Decreased or Low, a medium dose of B2 and/or NAD+ is used;
wherein there is no requirement that the switching of the first sub-module to the seventh sub-module shall be executed in order. That is, there is no need to switch the sub-modules in the order of first, second, third, fourth, fifth, sixth and seventh, e.g., the second sub-module can be executed first, then switch to the seventh sub-module, then switch to any of the remaining modules until all of these modules are executed.

In some preferred embodiments, the GMDAI personalized health formula system further comprises:
(0) a data input module: detected levels of at least two markers in the gene-regulation pathways, metabolic pathways and/or signal transduction pathways obtained from an individual sample are input;
and/or,
(4) a formula output module: type and dosage of the supplement determined by the formula finalization module is output to, for example, a printer.

Preferably, the individual sample is from saliva, blood, urine or dried blood spots.

In order to solve the technical problems described above, the second technical solution of the present invention is: a computer-assisted GMDAI personalized health recommendation method, which comprises the following steps:

(1) performing a pathway decision algorithm, which realizes the function of the pathway decision module of the GMDAI personalized health formula system of the first technical solution of the present invention, so as to make a decision to increase or decrease one or more of the markers;

(2) executing a supplement intervention algorithm, which utilizes the decision provided by the pathway decision algorithm of (1) and runs the supplement intervention module of the GMDAI personalized health formula system of any one of the first technical solution of the present invention, so as to generate personalized supplement intervention formula.

Preferably, after the first intervention, the levels of each marker in the biological pathways are evaluated again, and the supplement intervention algorithm is used to further optimize the type and dosage of supplements for long-term intervention.

More preferably, the GMDAI personalized health recommendation method further comprises the following steps:

(3) executing a formula finalization algorithm for the optimization of the personalized supplement formula, wherein the optimization comprises the following steps:

(i) removing duplicate supplements; and/or, (ii) selecting a lower dose if there is a conflict in the dosage of the supplements.

Even more preferably, the GMDAI personalized health recommendation method further comprises the following steps:

(0) inputting data: inputting the detected levels of at least two markers from the gene-regulation pathways, metabolic pathways and signal transduction pathways obtained from individual samples using the data input module;

and/or, (4) outputting formula: outputting a personalized supplement formula optimized by the formula finalization algorithm to, for example, a printer, using the formula output module.

In order to solve the technical problems described above, the third technical solution of the present invention is: a non-transitory computer-readable medium, wherein the computer-readable medium stores a computer program, and when the computer program is executed by a processor, it can implement function of the GMDAI personalized health formula system of the first technical solution of the present invention.

In order to solve the technical problems described above, the fourth technical solution of the present invention is: a non-transitory computer-readable medium, wherein the computer-readable medium stores a computer program, and when the computer program is executed by a processor, it can implement the GMDAI personalized health recommendation method of the second technical solution of the present invention.

In order to solve the technical problems described above, the fifth technical solution of the present invention is: a device for recommending personalized health formula based on genetic and metabolic data, which comprises:

(i) the computer-readable medium of the third technical solution of the present invention;

(ii) a processor, for executing a computer program to implement function of the GMDAI personalized health formula system of the first technical solution of the present invention.

In order to solve the technical problems described above, the sixth technical solution of the present invention is: a device for recommending personalized health formula based on genetic and metabolic data, which comprises:

(i) the computer-readable medium of the third technical solution of the present invention;

(ii) a processor, for executing a computer program to implement steps of the GMDAI personalized health recommendation method of the second technical solution of the present invention.

On the basis of conforming to common knowledge in the art, the preferred conditions as defined above can be combined randomly to obtain preferred embodiments of the present invention.

All supplements used in the present invention are commercially available.

The positive and progressive effects of the present invention are as follows:

The present invention pioneered BPO, designed and detected unique combinations of genetic and metabolic markers, processed and sorted data using bioinformatics, and used BPO to design types and dosages of supplements for personalized intervention. The algorithm developed by the present invention can combine obtained biological data (i.e. detected levels of selected biomarkers) to generate personalized intervention formulas (including form, dosage and method of use of individual supplements).

One example of the GMDAI personalized health formula system of the present invention is GMDAI personalized cell detoxification system, which overcomes the time-consuming, and inherently biased manual interpretation of multiple interlinked biomarkers. This automated evaluation also decreases the cost and offers quick and accurate guidance for personalized intervention.

DETAILED DESCRIPTION OF THE PREFERRED EMBODIMENT

Figure 1:
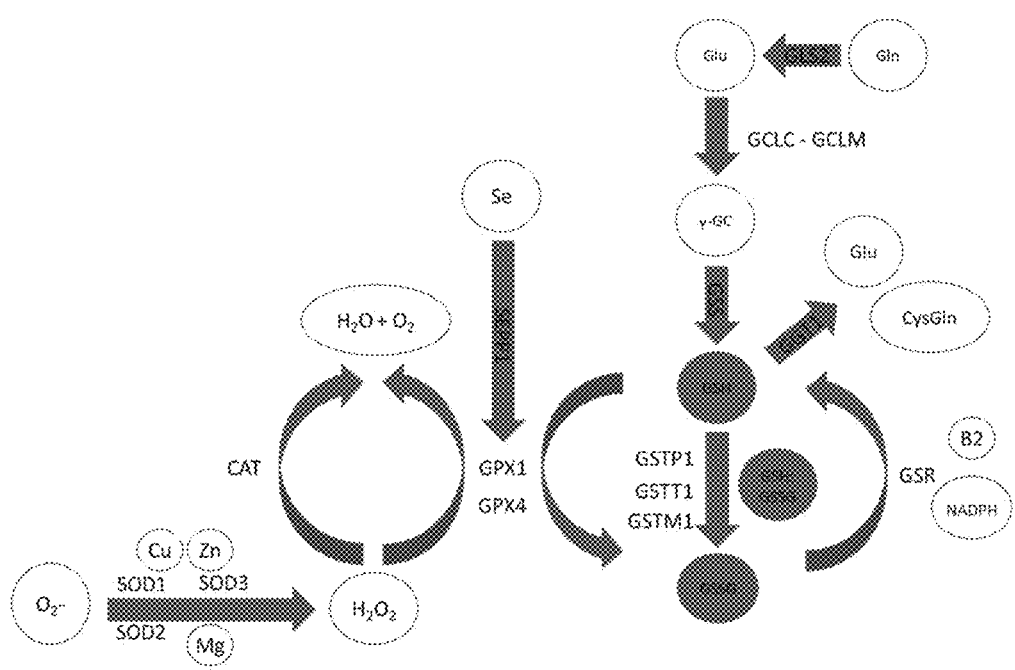
FIG. 1 illustrates a schematic diagram of the personalized cellular detoxification of through the trans-sulfuration biologic pathway utilized by GMDAI.

Biological pathway omics (BPO) is a new term that the inventor pioneered and further developed. BPO is based on the biological pathway theory. This is a unique innovation and invention that applies the concepts of three major biological pathways (metabolic, gene-regulation and signal transduction pathways) to the development of unique genetic and small molecule biomarker testing for the evaluation of human health, and for formulation of personalized supplementation intervention. The inventor has developed novel algorithms to associate the related genotypic and phenotypic data to generate a personalized intervention formula. The whole process of the present invention, starting with biomarker testing and continuing through the data integration, to the type and dosage of supplements, and then to the generation of personalized intervention formula, is named Genetic and Metabolic Data Associated Intervention (GMDAI), which can be applied to all available biological pathways.

Each Genetic and Metabolic Data Associated Intervention (GMDAI) product is a combination of genetic and metabolic test panels, and the evaluation of all obtained testing results by proprietary algorithm for personalized intervention plan. The genetic panels test for individual Single Nucleotide Polymorphisms (SNPs) and mutations, and metabolic panels focus on various metabolites typically participating in one or several related metabolic pathways. For each individual, the inventor collects a biological sample (saliva, blood, urine or dried blood spot) and tests metabolic as well as genetic panel biomarkers. In return, the inventor generates a list of the test values for each of the biomarkers and applies an algorithm for automated biomarker evaluation and generation of personalized intervention plan. Metabolic markers reflect the current health status of an individual. Keeping the metabolic markers within the desirable concentration ranges is essential for disease prevention. However, two possible pitfalls can be identified with using the metabolic markers for evaluation of individuals' health in isolation:

i. There are many different supplements available as possible intervention for restoring optimal metabolic marker levels. These supplements differ greatly in form, dosages, and possible side-effects. Considering only the metabolic levels, it is difficult to choose the optimal intervention supplement(s) with appropriate personalized dosage.

ii. The common approach to selection of intervention mostly focuses on interpretation of metabolic markers in isolation without considerations of complex interplay between metabolites which establishes pathway homeostasis.

To our knowledge, there is currently no commercially available product, which would combine the testing and assessment of individual's genes as well as metabolites with co-enzymes which are connected via a biochemical pathway. The inventor has developed and validated a unique algorithm for each GMDAI product which enables to simultaneously evaluate multiple biomarkers, and propose personalized intervention comprising optimal supplementation plan and lifestyle changes.

For the purposes of personalized health and preventive medicine, it can be very challenging to make an unbiased decision on optimal personalized intervention (i.e. the best supplementation form and dosage) based on assessment of test values of multiple interlinked biomarkers. Commonly, there can be over 20 biomarkers evaluated in one GMDAI product. The manual evaluation process is not only biased but it is also costly and time-consuming.

Genetic and Metabolic Data Associated Intervention (GMDAI) is an intervention method which utilizes pathway knowledge and accurate measurements of key metabolic and genetic markers involved in a biochemical pathway. The pathway knowledge guides the intervention to restore and maintain homeostasis. A combination of the genetic and metabolic markers is used to guide the personalized intervention to choose the right form and dosage of supplements.

In summary, The GMDAI testing enables easy and reproducible interpretation of combined metabolic and genetic test panels, where each panel comprises of many individual biomarkers. This interpretation is used for provision of optimal personalized supplementation and lifestyle change plan. Consecutively, GMDAI is further used to repeat the testing and monitor the health improvement during and after the intervention.

Description of GMDAI Workflow:

1. Select the most relevant Single Nucleotide Polymorphisms (SNPs) and mutations of genes encoding enzymes, transporters and receptors in the metabolic and cell-signalling biochemical pathways according to BPO;

2. Select active metabolites, co-enzymes and cofactors in the chosen biological pathways based on the concept of the BPO, and the relevant scientific research as well as available in vitro and in vivo experimental data;

3. Combine the selected genetic, metabolic and co-enzyme biomarkers into a testing panel;

4. Obtain personal health information through a consultation with a customer or via a consulting healthcare provider;

5. Collect biological sample(s) from the customer and test all selected metabolic and genetic biomarkers;

6. Evaluate and score the acquired data using expertise and proprietary algorithm, and associate the genetic and metabolic test results with the type and dose of selected supplements using a proprietary algorithm to generate personalized intervention plan.

7. To compensate for the genetic variances that impact the encoded metabolic enzymes, transporters and signal-transduction proteins, a personalized supplementation plan comprising selected nutraceuticals with co-enzymes is used to restore and keep the natural homeostasis in the target biological pathways system.

8. Proprietary algorithms are used to automatically generate the personalized formulations of nutraceutical or supplement packages.

9. Release a personalized report containing a tailor-made supplementation and lifestyle intervention plan to customer or healthcare provider.

10. During the intervention period, provide follow-up metabolic testing of the GMDAI panel biomarkers for monitoring of metabolic biomarker changes and adjustment of the personalized supplementation formula based on these observed changes.

In summary, the invention includes:
- the novel term of biological pathway omics (BPO)
- a unique combination of metabolic and genetic biomarkers for automated personalized supplementation recommendations (including form, dosage and use of individual supplements)
- the evaluation can also include physical measurements (e.g. blood pressure, body composition, BMI), biomarker health ranges, and other clinical data (e.g. medical history, current medication)
- all details relating to the GMDAI algorithm—how it is constructed and how it is used for reliable biomarker evaluation, associating molecular assay data with types and doses of individual supplements to generate personalized intervention formulations.

GMDAI approach, as well as specific GMDAI applications. GMDAI personalized health formula includes, but is not limited to the following panels:

GMDAI Methylation balance (according to methylation cycle metabolic pathway)

GMDAI Thyroid Health (according to thyroid hormone metabolic pathway)

GMDAI Neurotransmitter (according to neurotransmitter metabolic and signal transduction pathway)

GMDAI Adrenal Stress (according to adrenal hormone metabolic pathway)

GMDAI Detoxification (according to trans-sulfuration metabolic pathway)

GMDAI Hormonal Balance (according to male and female hormone metabolic pathways)

GMDAI Cardio Risk (according to methylation and folate metabolic pathways)

GMDAI Mental Health (according to methylation, folate and tetrahydrobiopterin (BH4) metabolic pathways)

GMDAI Joint Health (according to methylation, folate and partial trans-sulfuration metabolic pathways)

GMDAI Immunity Enhancing (according to methylation cycle metabolic pathway)

GMDAI Muscle Gain and Fat Loss (according to growth hormone signalling pathway), etc.

GMDAI Detoxification details are enclosed below to illustrate in detail the construction and application of GMDAI algorithm based on the trans-sulfuration biological pathway.

1. Trans-Sulfuration Biological Pathway

A schematic picture of the trans-sulfuration biological pathway is presented in FIG. 1 where individual genes as well as metabolic substrates and products are depicted. Altogether, seventeen genetic markers are simultaneously evaluated with three metabolic markers (two individual metabolite levels and a ratio of these two metabolites). Sections 1.1 and 1.2. below provide details for both genetic and metabolic markers.

FIG. 1: Trans-sulfuration biological pathway. Abbreviations next to or inside the arrows refer to genes involved in the pathway (see Table 1 for details of the individual genes). Abbreviations in the hollow circles refer to metabolites or their ratios or coenzymes. Abbreviations in the filled-in circles are the levels of assessed metabolites.

1.1 Genetic Marker Details

Table 1 lists all genes with selected SNPs and mutations examined in the trans-sulfuration biological pathway together with the options for detected genotypes for each marker and the resulting predicted enzymatic activity change for each of the genotype options.

TABLE 1

Genes involved in trans-sulfuration biological pathway with associated single nucleotide polymorphisms (SNPs) and estimated enzymatic activity changes for each genotype.

| Gene | SNP or mutation | Genotype | Enzyme Activity |
|---|---|---|---|
| GLS2 (glutaminase 2) | rs2657879 | AA | Decreased |
|  |  | AG | Normal |
|  |  | GG | Increased |
| GCLC (glutamylcysteine ligase catalytic subunit) | rs761142 | AA | Normal |
|  |  | AC | Decreased |
|  |  | CC | Low |
| GCLM (glutamylcysteine ligase modifier subunit) | rs41303970 | GG | Normal |
|  |  | GA | Decreased |
|  |  | AA | Low |
| GSS (glutathione synthetase) | rs3761144 | GG | Normal |
|  |  | GC | Decreased |
|  |  | CC | Low |
| GSR (glutathione reductase) | rs1002149 | GG | Normal |
|  |  | GT | Increased |
|  |  | TT | High |
| GSTP1 (Glutathione S-Transferase pi 1) | rs1695 | GG | Low |
|  |  | AG | Decreased |
|  |  | AA | Normal |
| GSTM1 (glutathione S-transferase M1) | Null mutation* | Present | Normal |
|  |  | Null mutation | Low |
| GSTT1 (glutathione S-transferase T1) | Null mutation* | Present | Normal |
|  |  | Null mutation | Low |
| GPX1 (glutathione peroxidase 1) | rs1050450 | GG | Normal |
|  |  | AG | Low |
|  |  | AA | Low |
| GPX4 (glutathione peroxidase 4) | rs713041 | TT | Decreased |
|  |  | CT | Normal |
|  |  | CC | Normal |
| SEPP1 (selenoprotein P1) | rs7579 | CC | Normal |
|  |  | CT | Increased |
|  |  | TT | Increased |
| SOD1 (super oxide dismutase 1) | rs10432782 | TT | Normal |
|  |  | GT | Increased |
|  |  | GG | High |
| SOD1 (super oxide dismutase 1) | rs1041740 | CC | Normal |
|  |  | CT | Decreased |
|  |  | TT | Low |
| SOD2 (super oxide dismutase 2) | rs4880 | AA | High |
|  |  | AG | Increased |
|  |  | GG | Normal |
| SOD3 (super oxide dismutase 3) | rs2536512 | GG | Normal |
|  |  | AG | Decreased |
|  |  | AA | Low |
| CAT (catalase) | rs769217 | CC | Normal |
|  |  | CT | Decreased |
|  |  | TT | Low |
| GGT1 (Gamma glutamyl transferase 1) | rs4820599 | AA | Normal |
|  |  | AG | Increased |
|  |  | GG | High |

*The GSTM1 and GSTT1 markers are not SNPs but null mutations which will cause gene deletion resulting in loss of protein function.

1.2 Optimal Health Ranges of Metabolic Markers

Figure 2:
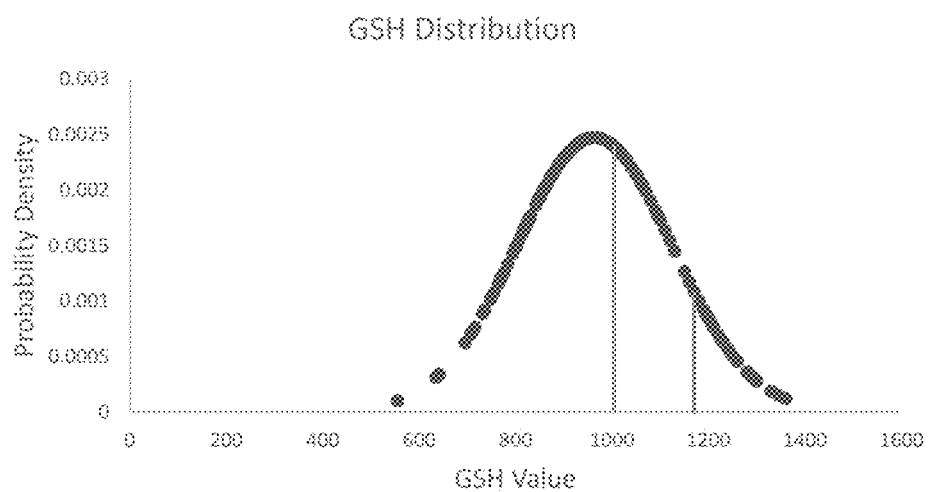
FIG. 2 illustrates normal distribution of GSH concentration values in a reference population with lower cutoff ($60^{th}$ percentile; light gray vertical line) and upper cutoff ($90^{th}$ percentile; dark gray vertical line) percentiles demarking the GSH level range for triggering personalized intervention algorithm.
Figure 3:
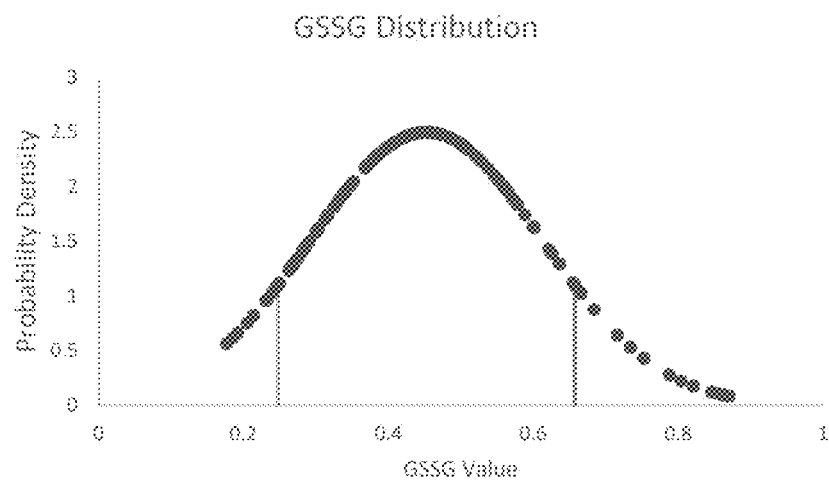
FIG. 3 illustrates normal distribution of GSSG values in a reference population with lower cutoff ($10^{th}$ percentile; light gray vertical line) and upper cutoff ($90^{th}$ percentile, dark gray vertical line) percentiles demarking the GSSG level range triggering personalized intervention algorithm.
Figure 4:
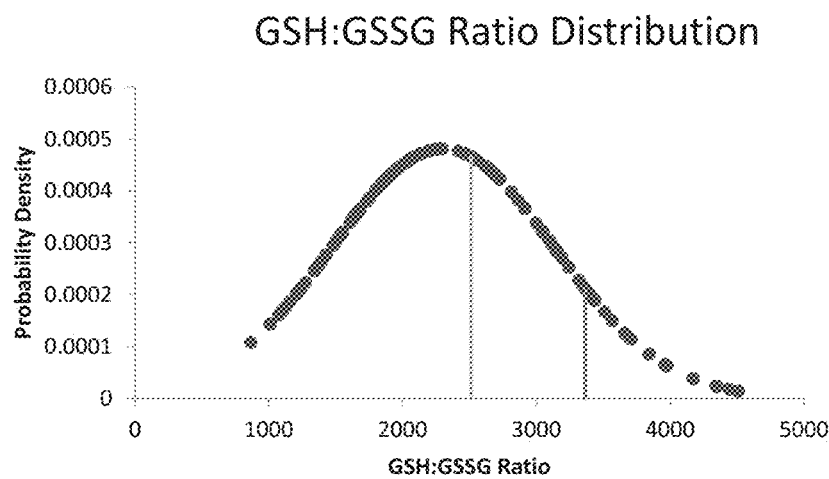
FIG. 4 illustrates normal distribution of the GSH:GSSG ratio values in a reference population with lower cutoff ($60^{th}$ percentile; light gray vertical line) and upper cutoff ($90^{th}$ percentile; dark gray vertical line) percentiles demarking the GSH:GSSG ratio level range triggering personalized intervention algorithm.

The common reference range used for metabolic markers is from $2.5^{th}$ percentile to $97.5^{th}$ percentile of the concentration value detected from a reference population. For GMDAI evaluation, optimal ranges are used instead of the reference ranges. The optimal health ranges are narrower than general reference ranges, and are designed based on biological functions of each of the individual metabolic markers. The optimal health ranges are calculated by an equation presented below (see Equation 1). Table 2 presents the optimal health ranges for metabolic markers involved in the detoxification pathway. FIGS. 2 to 4 depict the distribution of detected values of GSH, GSSG and GSH:GSSG ratio.

TABLE 2

Percentiles used for the determination of optimal health ranges for selected metabolic markers in detoxification pathway.

| Marker | Optimal health range |
|---|---|
| GSH (glutathione) | $60^{th}$ percentile to $90^{th}$ percentile |
| GSSG (glutathione disulfide) | $10^{th}$ percentile to $90^{th}$ percentile |
| GSH:GSSG ratio | $60^{th}$ percentile to $90^{th}$ percentile |

Note:
the percentiles used to determine the optimal health range for selected metabolic markers, which are used to trigger the detoxification pathway algorithm for generation of the personalized intervention plan.

FIG. 2: Normal distribution of GSH concentration values in a reference population with lower cutoff (60th percentile; in light gray) and upper cutoff (90th percentile; in dark gray) percentiles demarking the GSH level range triggering algorithm for personalized intervention generation. The horizontal axis represents GSH concentration value, and the vertical axis is the probability density of the normal distribution. The sample size, the average value (AVG), and the standard deviation (SD) are 188, 963.2, and 161.4, respectively. The percentiles are calculated by the Equation 1.

$$n^{th} \text{percentile} = AVG + SD \ast (z \text{ score of } n^{th} \text{ percentile}) \quad \text{Equation 1}$$

Equation 1: Equation for the calculation of percentiles used for determination of optimal health ranges. The z scores of $60^{th}$ and $90^{th}$ percentiles are 0.253 and 1.282, respectively. Thus, $60^{th}$ and $90^{th}$ percentiles of GSH are 1004.1 and 1170.1, respectively.

FIG. 3: Distribution of GSSG values in a reference population with lower cutoff ($10^{th}$ percentile; in light gray) and upper cutoff ($90^{th}$ percentile, in dark gray) percentiles demarking the GSSG level range for triggering algorithm used for generation of personalized intervention plan. The horizontal axis refers to GSSG concentration value, and the vertical axis is the probability density of the normal distribution. The sample size, the average value (AVG), and the standard deviation (SD) are 137, 0.453, and 0.160, respectively. The z scores of $10^{th}$ and $90^{th}$ percentiles are −1.282 and 1.282, respectively. Thus, the $10^{th}$ and $90^{th}$ percentiles of GSSG are 0.66 and 0.25, respectively.

FIG. 4: Distribution of the GSH:GSSG ratio values in a reference population with lower cutoff ($60^{th}$ percentile; in light gray) and upper cutoff ($90^{th}$ percentile; in dark gray) percentiles demarking the GSH:GSSG ratio level range for triggering the algorithm for generation of personalized intervention plan. The horizontal axis is the value for the GSH:GSSG ratio, and the vertical axis is the probability density of the normal distribution. The sample size, the average value (AVG), and the standard deviation (SD) are 135, 2301.5, and 829.2, respectively. The $60^{th}$ and $90^{th}$ percentiles of GSH:GSSG ratio are 2511.3 and 3364.5, respectively.

2. Verification of the Correlation Between Metabolic Markers

Even though the metabolic markers are directly linked through the metabolic pathway of interest, it is necessary to explore the correlation between these markers. Each metabolite is typically involved in multiple metabolic pathways and therefore a direct correlation between two markers in one metabolic pathway might sometimes not be observed. For intervention purposes, if a statistically significant correlation between metabolic markers is observed, as is the case for GSH and GSSG, an intervention addressing one of the markers is also likely to impact levels of the other marker. Table 3 shows that there is statistically significant correlation between GSH and GSSG metabolic markers. The correlation coefficient is 178.1283, and the p-value is smaller than 0.05, which indicates a statistically significant positive correlation between GSH and GSSG. The observed correlation is independent of gender and age. Therefore, it can be presumed that an intervention which increases GSH levels will also simultaneously increase GSSG levels.

TABLE 3

Correlation between GSH and GSSG

| | Coefficients | Standard Error | t Stat | P-value |
|---|---|---|---|---|
| Intercept | 968.7258 | 64.3194 | 15.06117 | 1.56E−30 |
| Age | −2.00746 | 1.021149 | −1.96589 | 0.051395 |
| Gender | −3.16267 | 27.60971 | −0.11455 | 0.908975 |
| GSSG | 178.1283 | 78.3406 | 2.273767 | 0.024582 |

Note:
Multiple regression among GSSG, GSH, age, and gender with GSH as the criterion variable.

3. Intervention Methods

After evaluation of scientific evidence, supplements suitable for effective intervention are selected for each GMDAI panel. For the detoxification pathway, supplements proven to effectively influence metabolic marker levels or support function of related enzymes are listed in Tables 4 and 5 respectively.

3.1 Supplements That Increase Metabolic Markers Directly or Indirectly

TABLE 4

List of supplements that directly or indirectly influence the levels of the metabolic markers involved in the detoxification pathway.

| Supplement | Abbreviation | Function |
|---|---|---|
| Glutathione | GSH | Increase GSH level and GSH:GSSG ratio |
| N-Acetyl Cysteine | NAC | Increase GSH level and GSH:GSSG ratio |

3.2 Supplements That Affect the Activity of Related Enzymes

TABLE 5

List of supplements that can modulate activity of enzymes involved in the detoxification pathway.

| Supplement | Abbreviation | Function |
|---|---|---|
| Isothiocyanate | ITC | Increase activities of GSTM1, GSTP1, GSTT1, and GCLC |
| Alpha-lipoic acid | ALA | Co-factor of GPx1 |
| Vitamin C | VC | Co-factor of SOD2 |
| Vitamin E | VE | Co-factor of SOD1 and SOD3 |
| Nicotinamide adenine dinucleotide | NAD+ | Precursor of nicotinamide adenine dinucleotide phosphate (NADPH) which is co-enzyme of GSR |
| Vitamin B2 | B2 | Co-enzyme of GSR |
| Selenium | Se | Co-factor of GPx1 |

TABLE 5-continued

List of supplements that can modulate activity of enzymes involved in the detoxification pathway.

| Supplement | Abbreviation | Function |
|---|---|---|
| Ubiquinol | Q10H2 | Decrease expression and activity of GGT1 |
| Zinc | Zn | Co-factor of SOD1 and SOD3 |
| Copper | Cu | Co-factor of SOD1 and SOD3 |
| Manganese | Mn | Co-factor of SOD2 |

4. GMDAI Algorithm

The individual SNPs and mutations will affect the activities of enzymes, transporters and receptors which drive the biomolecular reactions in cells. The detected levels of metabolites from related metabolic pathways reflect the individual's current health status. The inventor tested the biomarkers from both metabolic and genetic panels and, in turn, obtain a list of the test values of each biomarker. A value of each of the biomarker can potentially be under, within or over reference range as defined by the scientific consensus. To optimize and maintain metabolic processes in human body, we apply an internally developed algorithm to assess and associate the genetic and metabolic data, and to generate the personalized intervention plan. This whole workflow is called Genetic and Metabolic Data Associated Intervention (GMDAI) and is the core focus of the present application.

4.1 GMDAI Core Principles

For each for the GMDAI products, the following core principles can be presumed:

i. Genetic and metabolic biomarkers are related via biochemical pathways.

ii. The detected level of a metabolic biomarker is evaluated as Normal (within the optimal range), Low (Lower than the optimal range), or High (higher than the optimal range). The activity of a genetic biomarker is assigned as High, Increased, Normal, Decreased, or Low based on the detected polymorphisms.

iii. The genetic biomarker suggests how the activity of the corresponding enzyme, transporter or receptor is affected.

iv. Enzymatic activity can be modulated by supplementation of the enzyme's cofactor(s). The supplementation route, dosage and the specific form of supplements for each individual are decided by proprietary algorithm based on the results of their genetic and metabolic biomarker test results.

v. In summary, GMDAI algorithm processes an individual's genetic and metabolic data to output a personalized supplementation plan.

Figure 5:
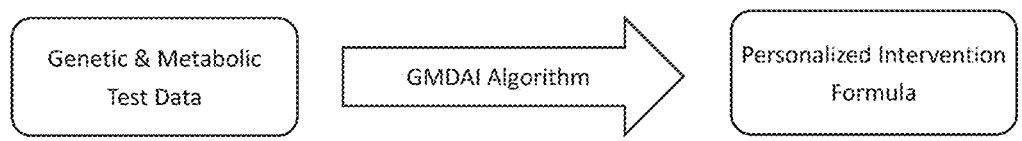
FIG. 5 illustrates scheme of the use of GMDAI algorithm.

FIG. 5 illustrates the scheme of the use of GMDAI Algorithm. The data obtained from analysis of genetic and metabolic markers are evaluated by the GMDAI Algorithm to obtain a personalized intervention formula.

FIG. 5 shows the algorithm of a generic GMDAI personalized health formula, which takes metabolic markers as an example and executes an algorithm to increase or decrease metabolic marker levels depending on whether the metabolic marker levels are below or above the optimal range of cutoff values, and consequently adding supplements that help to optimize the metabolic markers. The level of enzymatic activity is estimated by testing genetic polymorphism, thereby determining the dose levels of supplements. The selected supplements and coenzymes are used to compensate or regulate the different activities of metabolic enzymes influenced by polymorphisms in the encoding genes, in addition to maintaining normal levels of active metabolites in the pathway. The aim of the whole formula is to maintain the dynamic balance of the biological systems in the selected biological pathway.

4.2 Implementing Steps For Development of the GMDAI Algorithm

Each GMDAI algorithm is constructed via the following implementation steps:

i. Build a pathway model containing both genetic and metabolic biomarkers.

ii. Convert the pathway knowledge and usage of supplements into an algorithm.

iii. Build a database to store genetic and metabolic data.

iv. Implement the algorithm in a programming language.

In the example given here for GMDAI Detoxification, the algorithm is based on a comprehensive understanding of correlations and interactions among the genetic markers and metabolic markers involved in the detoxification pathway.

The algorithm input is a set of detected values for selected genetic markers and metabolic markers, and the output is a personalized intervention formula consisting of a list of recommended supplement forms and their dosages.

In general, the GMDAI algorithm includes one Pathway Decision Algorithm, at least two Marker Intervention Algorithms, and one Formula Finalization Algorithm. The Pathway Decision Algorithm provides Intervention formulations or protocols (what to do) for selected areas of human health, and contains the thresholds of metabolic markers that trigger the intervention algorithm for different metabolic pathways. The Marker Intervention Algorithms gives optimal forms and dosages of supplements to achieve the Intervention targets (how to do it). The whole algorithm can be divided into four steps which are described for the trans-sulfuration biological pathway below.

4.3 Evaluation of Metabolic and Genetic Markers

The detected level of each of the metabolic markers evaluated in the trans-sulfuration biological pathway is assigned one of reference values: Normal (detected value falls within the optimal range), Low (detected value is lower than the optimal range), or High (detected value lies above the optimal range). The activity of a genetic biomarker is assigned a value of High, Increased, Normal, Decreased, or Low based on the detected polymorphisms described in Table 1. If a gene has more than one marker tested, then its activity level is the average level of these markers.

For calculation purposes, each genetic marker is assigned an artificial value ranging from 2 to −2 (see Table 6). An example of calculation of overall gene activity is given in Table 7.

TABLE 6

Five possible relative values used for the evaluation of the genetic markers.

| Genetic marker level* | Assigned artificial value |
|---|---|
| High | 2 |
| Increased | 1 |
| Normal | 0 |
| Decreased | −1 |
| Low | −2 |

*increased GGT1 activity has a negative effect on GSH utilization. Therefore, a negative number will be used in the calculations.

TABLE 7

Example of gene activity calculations.

| Gene | SOD1 | | SOD2 |
|---|---|---|---|
| SNP | rs10432782 | rs1041740 | rs4880 |
| Genotype | TT | TT | GG |

TABLE 7-continued

Example of gene activity calculations.

| SNP result | Normal | Low | Normal |
|---|---|---|---|
| Gene result | | Decreased | Normal |

4.4 Intervention Targets Derived From the Pathway Decision Algorithm

The Intervention targets are mainly determined by metabolic levels. Basically, the aim is to increase the metabolic marker level if it is lower than the optimal range or reduce its level if it is higher than the optimal range. To keep the homeostasis, one intervention target may simultaneously trigger another intervention target. For example, when GSH level is Low, and GSSG level is Normal, the intervention target is to increase GSH level but also simultaneously reduce GSSG. The purpose of reducing GSSG is to maintain homeostasis.

4.5 Triggering of a Marker Intervention Algorithm by Each Intervention Target i. GSH Intervention Algorithm GSH or NAC supplements can be used for the increase of endogenous GSH levels of the tested individual. The choice between these two types of supplements can be guided by the evaluation of genetic markers. Different people have different responses to the same supplement and their genetic variation is one of the key reasons. GSS, GCLC, GCLM, and GLS2 genes are involved in the synthesis of GSH. If the lowest activity among these four genes is higher than Decreased, then NAC supplementation is preferred to GSH-based intervention, and vice versa. The dose of NAC is determined by activities of GSTM1, GSTP1, GSTT1, GSR, GSS, GCLC, GCLM and GLS2. The dose of GSH is determined by activities of GSTM1, GSTP1, GSTT1, and GSR. Other possible supplements for improvement in the trans-sulfuration biological pathway include ITC, Se, Zn, Cu, Mn, Q10H2, VC and VE which can regulate the activity of enzymes in the pathway, are used to enhance the function of GSH or NAC. See details in FIG. 10, FIG. 11 and FIG. 12.

ii. GSSG Intervention Algorithm

Vitamin B2 and NAD+, co-factors of GSR, are used to enhance the conversion from GSSG to GSH. The doses of vitamin B2 and NAD+ are determined by the activity of GSR.

4.6 Formula Finalization Algorithm

The personalized intervention formula is finalized by the application of the Formula Finalization Algorithm which serves the follow two purposes:

i. Remove duplicate supplement recommendations;

ii. If there is a conflict in treatment dosages, use the lower dose of the supplement.

Example 1

This section provides a specific example of the GMDAI Detoxification testing before and after following the personalized intervention recommendation. Obviously, the genetic marker values do not change but after the personalized intervention an increase in detected GSH levels is expected.

Figure 6:
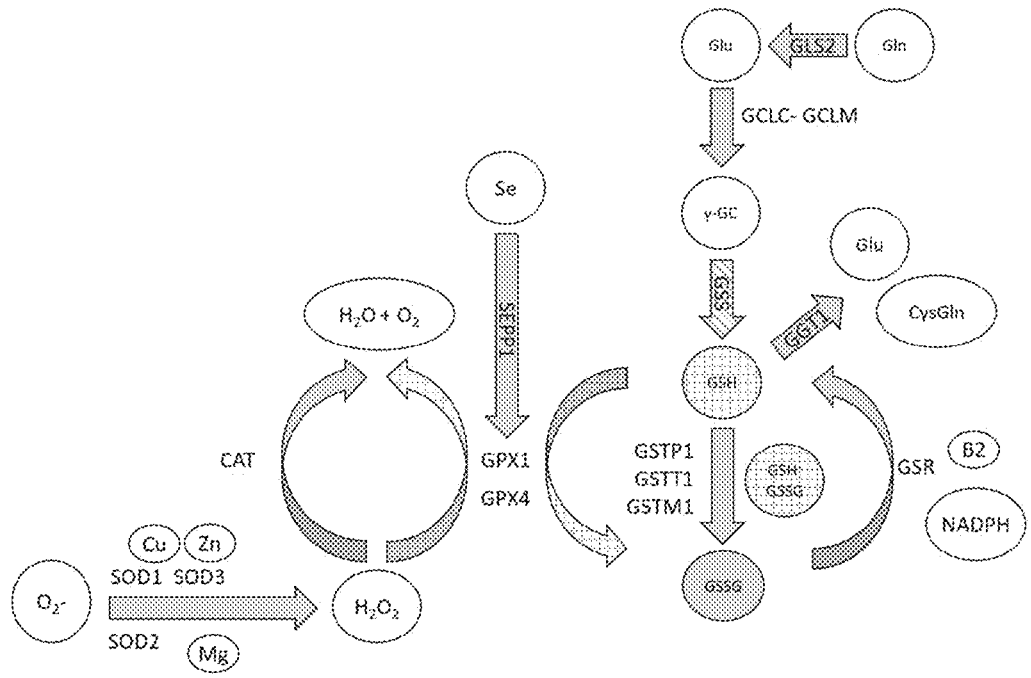
FIG. 6 illustrates an example of metabolic and genetic marker testing transposed onto the detoxification pathway prior to application of GMDAI evaluation and suggestion of personalized intervention.

FIG. 6: An example of the metabolic and genetic marker testing transposed onto the detoxification pathway prior to application of GMDAI evaluation and suggestion of personalized intervention. Both GSH and GSH:GSSG ratio are below their respective optimal ranges and therefore are represented in yellow. Genetic marker associated with function of GSS gene was assigned High impact, and GPX1 and GPX4 are expected to have Increased impact. In FIG. 6, filled arrows indicate that the gene-encoding metabolic enzyme activity is normal; checkered arrows indicate that the gene-encoding metabolic enzyme activity is affected by detected gene polymorphism(s), and is therefore decreased; dashed arrows indicate that the gene-encoding metabolic enzyme activity is strongly affected by detected gene polymorphism(s), and is therefore substantially decreased. Circles represent metabolites or their ratios, or coenzymes. A filled circle indicates a normal metabolite level, and checkered circle indicates a suboptimal metabolite level.

TABLE 8

Example of personalized formula

| Supplements | Dose |
|---|---|
| GSH | Low |
| Selenium | Medium |
| Zinc | Low |
| Copper | Low |
| Manganese | Low |
| B2 | Medium |
| NAD+ | Medium |
| Isothiocyanate | Low |
| Q10H2 | Low |

Figure 7:
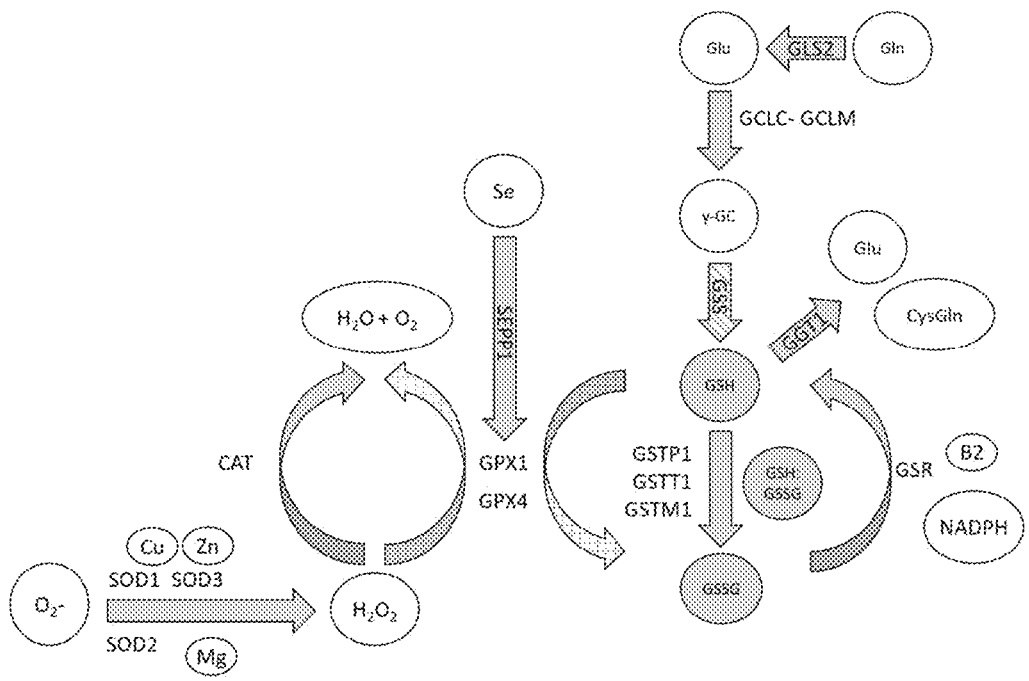
FIG. 7 illustrates an example of expected changes following the personalized intervention generated by the GMDAI program.

FIG. 7: An example of expected changes following the personalized intervention derived by the GMDAI procedure. The genetic markers stay constant but due to the intervention, the values of GSH and GSH:GSSG ratio return within optimal range. In FIG. 7, filled arrows indicate that the gene-encoding metabolic enzyme activity is normal; checkered arrows indicate that the gene-encoding metabolic enzyme activity is affected by the detected gene polymorphism(s) and is therefore decreased; dashed arrows indicate that the gene-encoding metabolic enzyme activity is strongly affected by detected gene polymorphism(s) is therefore substantially decreased. Circles represent metabolites or their ratios, or coenzymes. A filled circle indicates a normal metabolite level, and a checkered circle indicates a suboptimal metabolite level.

Figure 8:
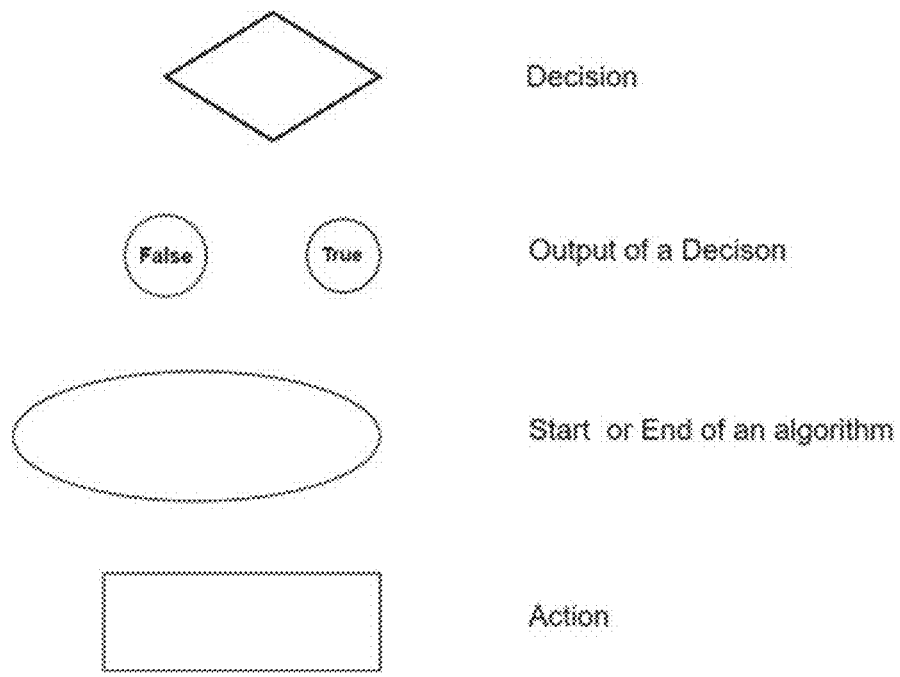
FIG. 8 illustrates legend for meanings of symbols used in all below presented diagrams.

FIG. 8: Legend for meanings of symbols used in all below presented diagrams. An action can be an Intervention target, a selection of the form or dose of a supplement, an analysis of gene activities, or a trigger for other actions.

Figure 9:
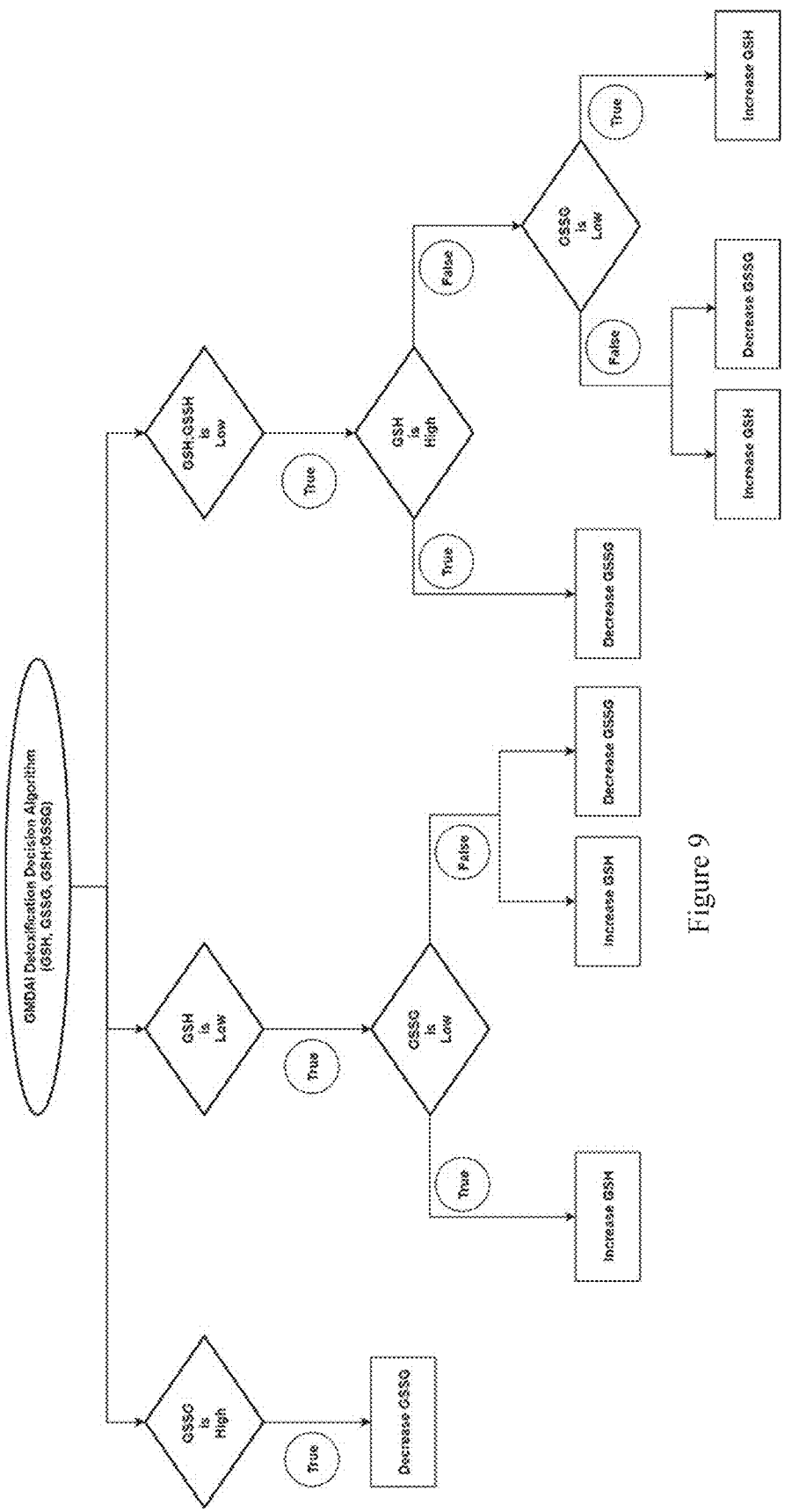
FIG. 9 illustrates GMDAI personalized cellular detoxification decision algorithm of the trans-sulfuration biological pathway.

FIG. 9: GMDAI Pathway Decision Algorithm in trans-sulfuration biological pathway—this algorithm is based on the optimal ranges of GSH, GSSG, and GSH:GSSG ratio. There are two possible intervention targets, Increase GSH and Decrease GSSG. Increase GSH will be triggered when GSH is assigned as Low, or GSH:GSSG ratio is assigned as Low and GSH level is not assigned as High. Decrease GSSG will be triggered when GSSG is assigned as high, GSH: GSSG ratio is assigned as Low and GSSG is not assigned as Low, or GSH is assigned as Low and GSSG is not assigned as Low.

Figure 10:
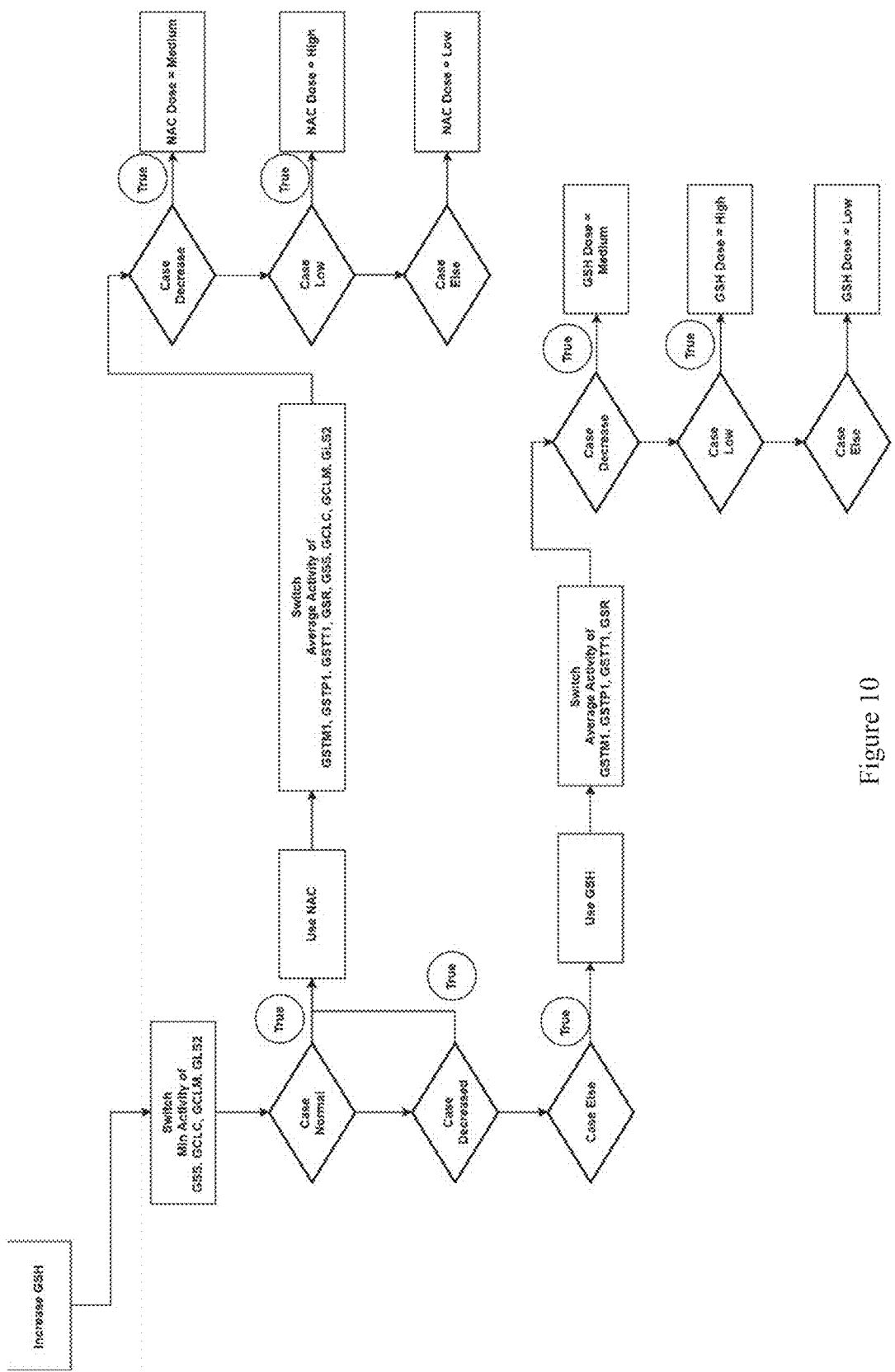
FIG. 10 illustrates the algorithm for evaluating gene activity and adjusting dosages of supplements when increasing GSH—part 1.

FIG. 10: GSH Intervention Algorithms—part 1. NAC is a precursor of GSH. GLS2, GCLC, GCLM, and GSS are involved in the synthesis of GSH. If minimal activity among the four genes is Normal or Decreased, then NAC will be used to increase the GSH level. The dose of NAC is determined by genes involved in the synthesis and utilization of GSH, including GSS, GCLC, GCLM, GLS2, GSTM1, GSTP1, GSTT1, and GSR. The dose of GSH is determined by genes involved in its utilization, including GSTM1, GSTP1, GSTT1, and GSR.

Depending on the type of the supplement and the internationally recognized guidelines for supplementation, the recommended dose of each supplement can range from tens to thousands of mg (or mcg). High, medium and low doses generally differ by a factor of two, for example, low means 20 mg, medium means 40 mg and high means 80 mg. The doses of different supplements in the present invention are determined by three factors: 1) Reference Dietary Allowance (RDA); 2) Upper Limit of Nutrient Allowance (UL); and 3) the dose of commercially available supplements. Of these, 1) and 2) are internationally recognized standards and are referenced as follows.

Institute of Medicine (US) Subcommittee on Interpretation and Uses of Dietary Reference Intakes; Institute of Medicine (US) Standing Committee on the Scientific Evaluation of Dietary Reference Intakes. Washington (DC): National Academies Press (US); 2000.

Reference to "Webmd" article "vitamins and supplements vitamins minerals how much should you take"

Reference to "FDA" article "food new nutrition facts label daily value new nutrition and supplement facts labels"

Figure 11:
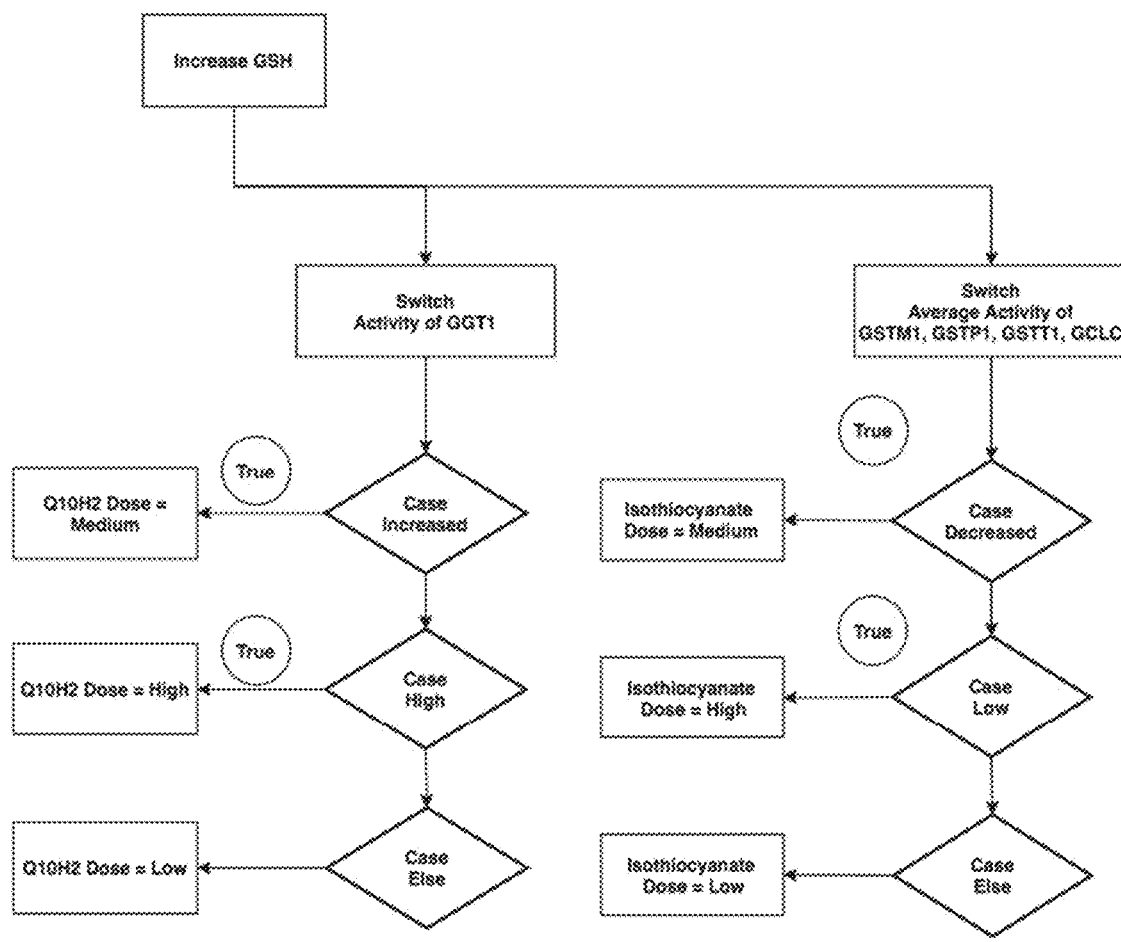
FIG. 11 illustrates the algorithm for evaluating gene activity and adjusting dosages of supplements when increasing GSH—part 2.

FIG. 11: GSH Intervention Algorithms—part 2. When Increase GSH is triggered, sulforaphane and Q10H2 will be used as supplements to enhance the utilization of GSH.

Figure 12:
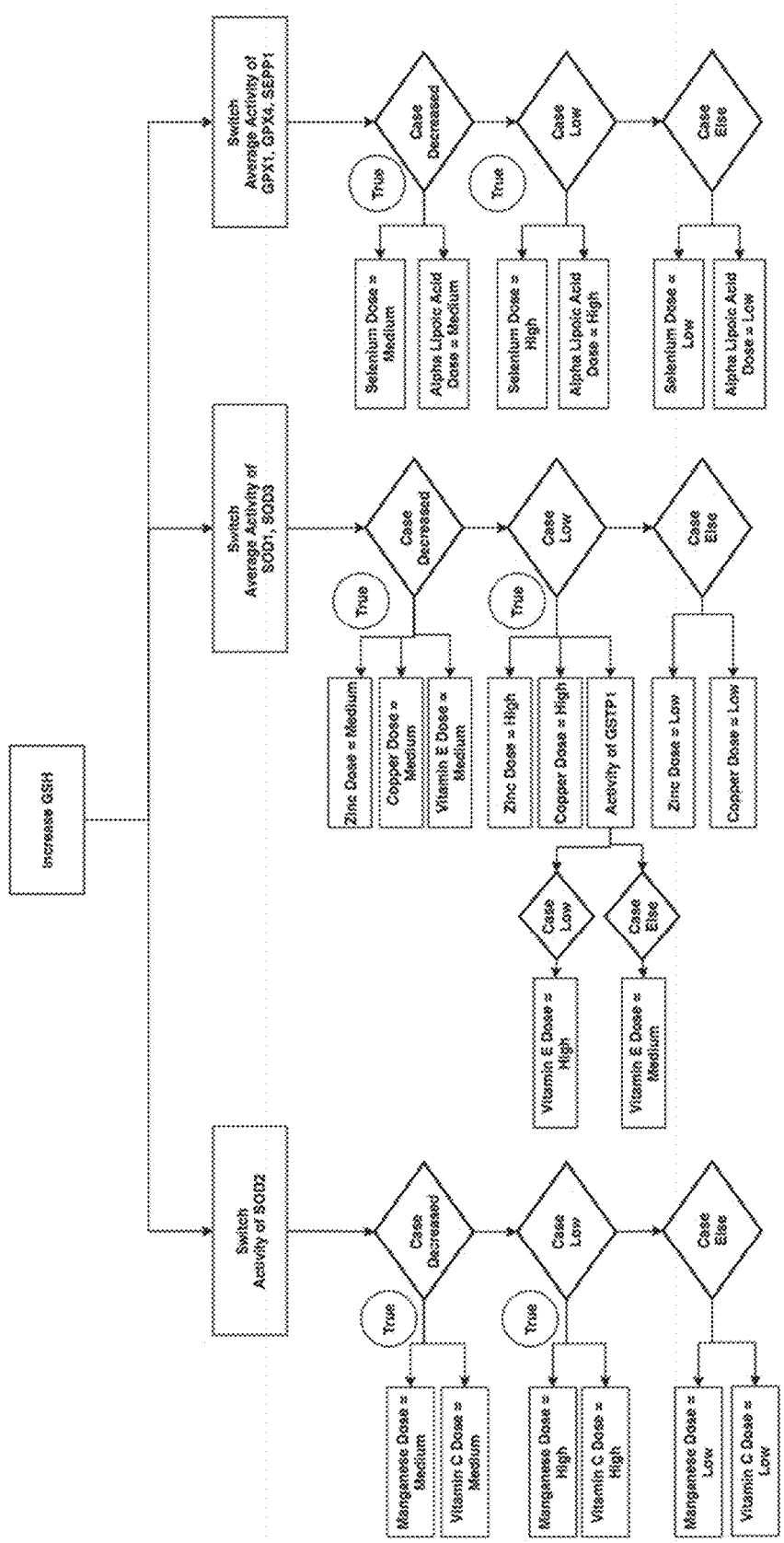
FIG. 12 illustrates the algorithm for evaluating gene activity and adjusting dosages of supplements when increasing GSH—part 3.

FIG. 12: GSH Intervention Algorithms—part 3. When Increase GSH is triggered, selenium, zinc, copper, and manganese will be used to enhance the utilization of GSH.

Figure 13:
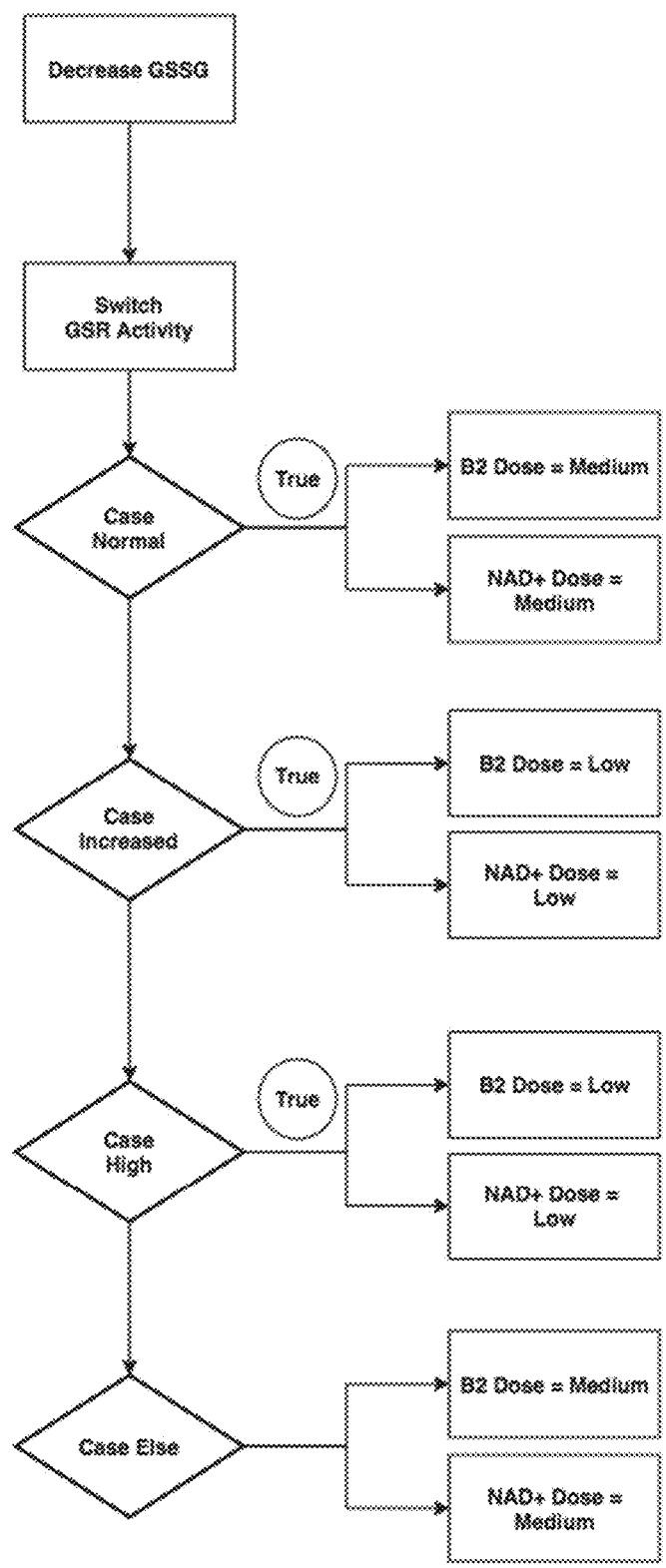
FIG. 13 illustrates the algorithm for evaluating gene activity and adjusting dosages of supplements when decreasing GSSG.

FIG. 13: Flow chart of the GSSG Intervention Algorithms. The variation of GSR gene has a beneficial effect on conversion from GSSG to GSH. Therefore, there is no High dose option for the associated co-enzymes.

Figure 14:
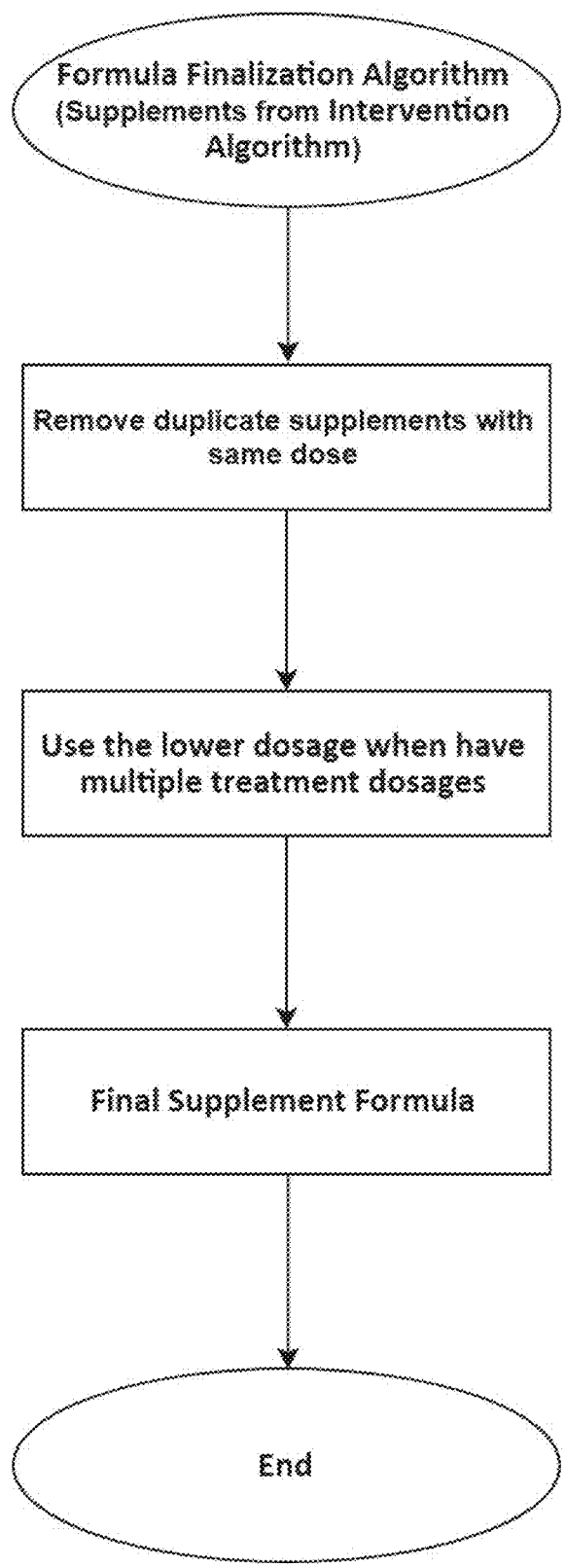
FIG. 14 illustrates a flow chart of the formula finalization algorithm to optimize the personalized supplement plan.
Figure 15:
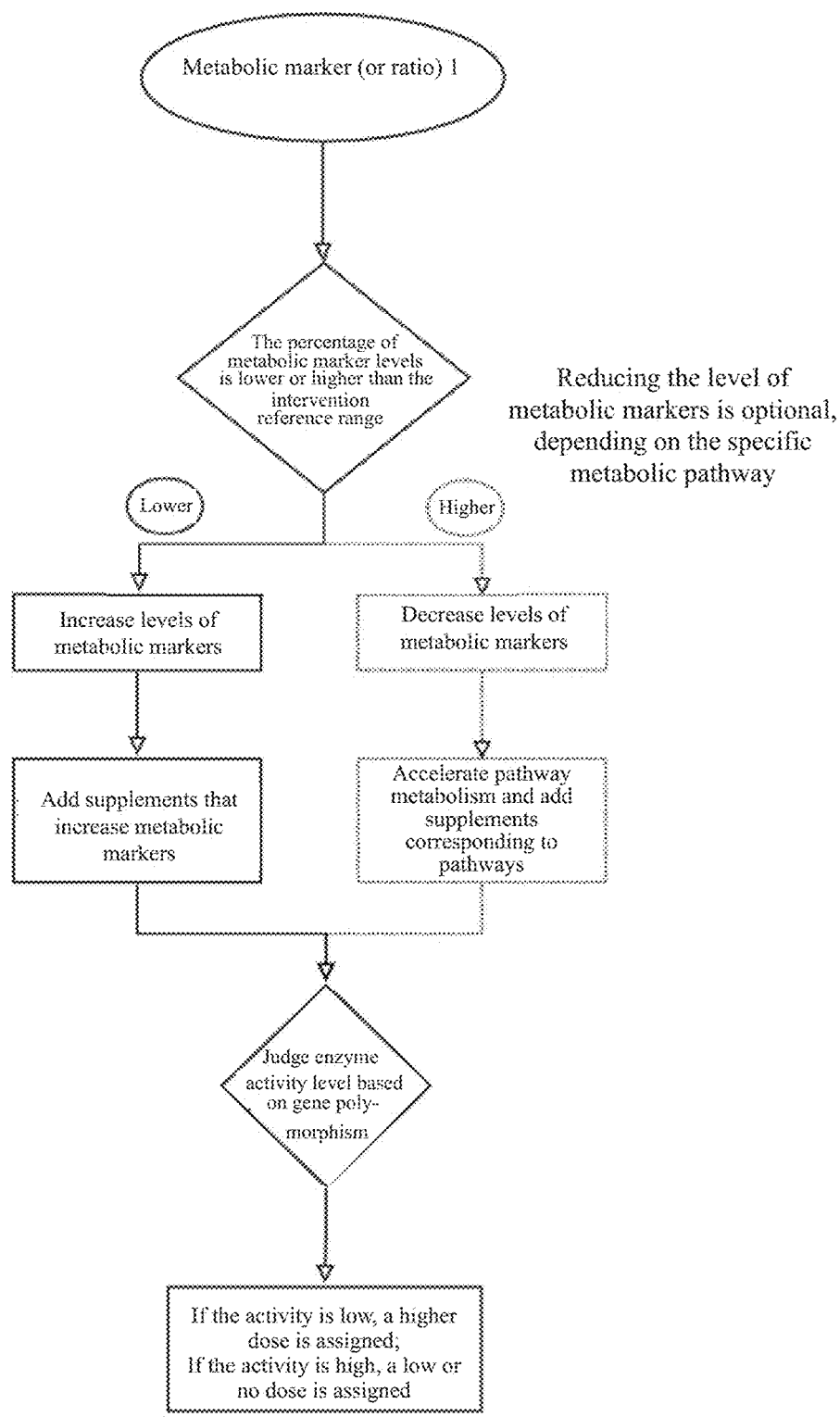
FIG. 15 illustrates the algorithm for a generic GMDAI personalized health formula.

FIG. 14: A flow chart describing steps involved in the Formula Finalization Algorithm.

Example 2

This Example provides a computer-readable medium having a computer program stored thereon, and when the program is executed by a processor, the function of the GMDAI personalized health formula system in Example 1 of the present invention is implemented.

Wherein, the readable medium can include, but is not limited to, a portable disk, a hard disk, random access memory, a read-only memory, an erasable programmable read-only memory, an optical storage device, a magnetic storage device or any suitable combination of the media described above.

In a possible embodiment, the present invention can also be implemented in the form of a program product comprising program code, and when the program product is run on a terminal device, the program code is used to make the terminal device execute the step of implementing the GMDAI personalized health recommendation method.

The program code for executing the present invention can be written in any combination of one or more programming languages, which can be completely executed on the user device, partially executed on the user device, executed as an independent software package, partially executed on the user device, partially executed on the remote device or completely executed on the remote device.

Example 3

This Example provides an electronic device, which can be represented in the form of a computing device (e.g. a server device) comprising a memory, a processor and a computer program stored in the memory and running on the processor, wherein the processor implements the GMDAI personalized health recommendation method when executing the computer program.

Figure 16:
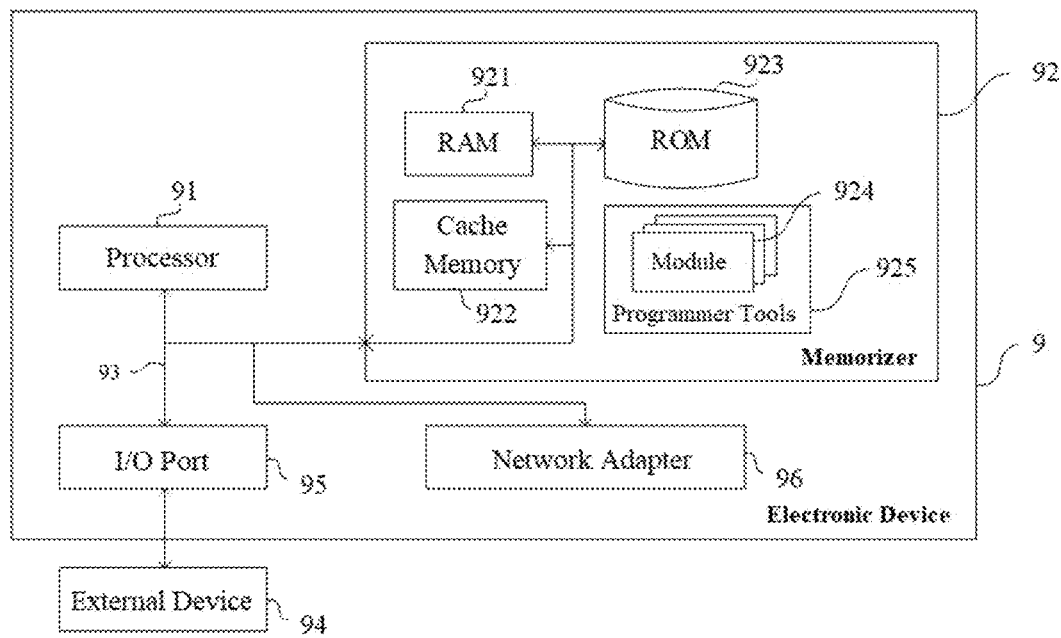
FIG. 16 illustrates a schematic structural diagram of an electronic device according to Example 3 of the present invention.

FIG. 16 illustrates a schematic diagram of the hardware structure of this Example, and the electronic device 9 specifically includes:

At least one processor 91, at least one memory 92, and a bus 93 for connecting different system components (including the processor 91 and the memory 92).

The bus 93 includes a data bus, an address bus and a control bus.

The memory 92 includes volatile memory such as random access memory (RAM) 921 and/or cache memory 922, and may further include read only memory (ROM) 923.

The memory 92 also includes a program/utility 925 having a set of (at least one) program modules 924 including but not limited to an operating system, one or more application programs, other program modules and program data, and each or some combination of these examples may include the implementation of a network environment.

The processor 91 executes various functional applications and data processing by running the computer program stored in the memory 92, such as the GMDAI personalized health recommendation method in Example 1 of the present invention.

The electronic device 9 may further communicate with one or more external devices 94 (e.g., keyboard, pointing device, etc.). This communication may be conducted through an input/output (I/O) port 95. Furthermore, the electronic device 9 can also communicate with one or more networks (such as a local area network (LAN), a wide area network (WAN) and/or a public network, such as the internet) through the network adapter 96. The network adapter 96 communicates with other modules of the electronic device 9 through the bus 93. It should be understood that although not shown in the figure, other hardware and/or software modules may be used in conjunction with the electronic device 9, including but not limited to microcode, device drives, redundant processors, external disk drive arrays, RAID (Disk Array) systems, tape drives, and data backup storage systems.

It should be noted that although several units/modules or sub-units/modules of electronic device are mentioned in the above detailed description, this division is only exemplary and not mandatory. In fact, according to the examples of the present invention, the features and functions of two or more units/modules described above can be embodied in one unit/module. On the contrary, the features and functions of one unit/module described above can be further divided into being embodied by a plurality of units/modules.

Although the specific embodiments of the present invention are described above, those skilled in the art should understand that these are only examples, and various changes or modifications can be made to these embodiments without departing from the principle and essence of the present invention. Therefore, the protection scope of the present invention is defined by the below claims.

What is claimed is:

1. A method for treating a person in an oxidative stress state using a Genetic and Metabolic Data Associated Intervention (GMDAI) personalized health formula, comprising:
   (1) executing a pathway decision,
   (2) executing a supplement intervention, and
   (3) executing a formula finalization to analyze genetic and metabolic markers data of a person in an oxidative stress state, to analyze correlation and interaction between the genetic and metabolic markers data, and to automatically generate a personalized supplementation formula to optimize and maintain related genetic and metabolic processes of the person;

wherein
- (A) the step of executing the pathway decision comprises:
  - (a) determining markers in three biological pathways comprising gene-regulation pathways, metabolic pathways and signal transduction pathways, the markers comprising genetic markers, metabolic markers and signal transduction markers;
  - (b) detecting a physiological level of each of the markers; and
  - (c) determining a decision of increasing or decreasing the physiological level of one or more of the markers by weighing detected physiological levels of all of the markers, wherein
    - (i) an increase or decrease of a physiological level of a marker depends on an optimal reference value into which an associated detected physiological level of the marker is assigned, and
    - (ii) in response to intervention of increase or decrease in the associated detected physiological level of the marker being applied, increasing or decreasing an associated detected physiological level of another marker to maintain a balance in a homeostasis of the person;
- (B) the step of executing the supplement intervention comprises:
  - (a) automatically generating a personalized supplementation formula based on the decision determined by the pathway decision; the supplementation formula comprises one or more supplements, the one or more supplements regulating activity of the genetic markers and affecting the detected physiological levels of the metabolic markers and the signal transduction markers; and
  - (b) providing the one or more supplements automatically generated in the personalized supplementation formula along with a dose of each of the supplements that is determined according to a type of the supplement;
- (C) the step of executing the formula finalization comprises:
  - (a) removing duplicate supplements; or
  - (b) selecting a lower dose if there is a conflict in a dosage of the supplements; and
- (4) administering the one or more supplements according to the personalized supplementation formula to the person;

wherein in the pathway decision, the physiological levels indicating activity of the genetic markers are assigned into optimal reference values of High, Increased, Normal, Decreased or Low according to a genotype of their SNPs;

in response to the detected physiological levels of the metabolic markers being below a lower cutoff percentile, between the lower cutoff percentile and an upper cutoff percentile or higher than the upper cutoff percentile, the detected physiological levels of the metabolic markers are respectively determined as Low, Normal and High;

and the High, Increased, Normal, Decreased or Low of the activity of a genetic marker is assigned as an artificial value of 2, 1, 0, −1 and −2 respectively; and in response to more than one marker of a gene is detected, the activity of the gene is an average value of these contributing markers;

wherein in the pathway decision, the percentile is calculated by a following equation:

$n^{th}$ percentile = AVG + SD*(z score of $n^{th}$ percentile)

wherein n is any value between 0 and 100, AVG represents average value of samples, SD represents standard deviation, and z is a probability value of the percentile in standard normal distribution model; the detected level of a metabolite is determined as Low, Normal and High based on the percentile and concentration of that marker;

wherein
in the pathway decision, the genetic markers of the gene-regulation pathways comprise glutaminase 2 (GLS2), glutamylcysteine ligase catalytic subunit (GCLC), glutamylcysteine ligase modifier subunit (GCLM), glutathione synthetase (GSS), glutathione reductase (GSR), Glutathione S-Transferase pi 1 (GSTP1), glutathione S-transferase M1 (GSTM1), glutathione S-transferase T1 (GSTT1), glutathione peroxidase 1 (GPX1), glutathione peroxidase 4 (GPX4), selenoprotein P1 (SEPP1), super oxide dismutase 1 (SOD1), super oxide dismutase 2 (SOD2), super oxide dismutase 3 (SOD3), catalase (CAT) and Gamma glutamyl transferase 1 (GGT1);

the metabolic markers of the metabolic pathways comprise glutathione (GSH), glutathione disulfide (GSSG) and GSH:GSSG ratio; and in the supplement intervention, the supplements that affect the detected levels of metabolic markers comprise glutathione (GSH) and N-Acetyl Cysteine (NAC), and the supplements that regulate the activity of genetic markers comprise isothiocyanate (ITC), alpha-lipoic acid (ALA), vitamin C (VC), vitamin E (VE), nicotinamide adenine dinucleotide (NAD+), vitamin B2, selenium (Se), ubiquinol (Q10H2), zinc (Zn), copper (Cu) and manganese (Mn);

wherein in the pathway decision, the activity of the genetic markers is determined based on the genotype corresponding to the SNPs of each gene as shown in a following table:

| Gene | SNP or mutation | Genotype | Enzyme Activity |
| --- | --- | --- | --- |
| GLS2 | rs2657879 | AA | Decreased |
| | | AG | Normal |
| | | GG | Increased |
| GCLC | rs761142 | AA | Normal |
| | | AC | Decreased |
| | | CC | Low |
| GCLM | rs41303970 | GG | Normal |
| | | GA | Decreased |
| | | AA | Low |
| GSS | rs3761144 | GG | Normal |
| | | GC | Decreased |
| | | CC | Low |
| GSR | rs1002149 | GG | Normal |
| | | GT | Increased |
| | | TT | High |
| GSTP1 | rs1695 | GG | Low |
| | | AG | Decreased |
| | | AA | Normal |
| GSTM1 | Null mutation | Present | Normal |
| | | Null mutation | Low |
| GSTT1 | Null mutation | Present | Normal |
| | | Null mutation | Low |
| GPX1 | rs1050450 | GG | Normal |
| | | AG | Low |
| | | AA | Low |
| GPX4 | rs713041 | TT | Decreased |
| | | CT | Normal |
| | | CC | Normal |

-continued

| Gene | SNP or mutation | Genotype | Enzyme Activity |
|------|-----------------|----------|-----------------|
| SEPP1 | rs7579 | CC | Normal |
| | | CT | Increased |
| | | TT | Increased |
| SOD1 | rs10432782 | TT | Normal |
| | | GT | Increased |
| | | GG | High |
| SOD1 | rs1041740 | CC | Normal |
| | | CT | Decreased |
| | | TT | Low |
| SOD2 | rs4880 | AA | High |
| | | AG | Increased |
| | | GG | Normal |
| SOD3 | rs2536512 | GG | Normal |
| | | AG | Decreased |
| | | AA | Low |
| CAT | rs769217 | CC | Normal |
| | | CT | Decreased |
| | | TT | Low |
| GGT1 | rs4820599 | AA | Normal |
| | | AG | Increased |
| | | GG | High; | and in the detected levels of the metabolic markers, the lower percentile cutoff of GSH is the $60^{th}$ percentile, and the upper percentile cutoff is the $90^{th}$ percentile; the lower percentile cutoff of the GSSG is the $10^{th}$ percentile, and the upper cutoff percentile is the $90^{th}$ percentile; and the lower percentile cutoff of the GSH:GSSG is the $60^{th}$ percentile, and the upper percentile cutoff is the $90^{th}$ percentile;

wherein in the pathway decision, the following assessments and decisions are made:
  (A) in response to GSH level being high, the decision is to decrease GSSG level;
  (B) in response to GSH level being low:
    (a) in response to GSSG level being low, the decision is to increase GSH level;
    (b) in response to GSSG level being normal or high, the decision is to increase GSH level and decrease GSSG level at the same time;
  (C) in response to GSH:GSSG being low:
    (a) in response to GSH level being high, the decision is to decrease GSSG level;
    (b) in response to GSH level being normal or low:
      (i) in response to GSSG level being normal or high, the decision is to increase GSH level and decrease GSSG level;
      (ii) in response to GSSG level being low, the decision is to increase GSH level; and in the supplement intervention:
  (A) in response to the decision being to increase level of GSH, the selection of NAC or GSH depends on the activity of the following four genes: GSS, GCLC, GCLM, and GLS2:
    (a) in response to a lowest activity of the four genes being higher than Decreased, NAC is selected as a supplement;
    (b) in response to the lowest activity of the four genes being lower than Decreased, GSH is selected as a supplement;
  (B) in response to the decision being to decrease GSSG level, B2 and NAD+ are selected as supplements;

and wherein in the supplement intervention,
  (A) the dose of NAC is determined by the activities of GSTM1, GSTP1, GSTT1, GSR, GSS, GCLC, GCLM and GLS2;
  (B) the dose of GSH is determined by the activities of GSTM1, GSTP1, GSTT1 and GSR; and
  (C) the doses of B2 and NAD+ are determined by the activity of GSR;

and wherein in the supplement intervention, in response to the decision being to increase GSH level, the decision also comprises use of ITC and Q10H2 as supplements, and use of selenium, zinc, copper, alpha-lipoic acid, vitamin E, vitamin C and manganese as supplements;

wherein in the supplement intervention, in response to the decision being to increase GSH level,
  (1) evaluating gene activity and adjusting dosages of supplements for maintaining levels of GSH by evaluating a minimum activity among the activities of GSS, GCLC, GCLM or GLS2, and:
    (A) in response to the minimum activity being Normal or Decreased, administering NAC as a supplement to the person; then, average activity of GSTM1, GSTP1, GSTT1, GSR, GSSS, GCLC, GCLM or GLS2 is determined:
      in response to the average activity being Decreased, administering a medium dose of NAC as a supplement to the person;
      in response to the average activity being Low, administering a high dose of NAC to the person;
      in response to the average activity being Normal, Increased or High, administering a low dose of NAC as a supplement to the person;
    (B) in response to the minimum activity being Increased or High, administering GSH as a supplement to the person; then, average activity of GSTM1, GSTP1, GSTT1 or GSR is determined:
      in response to the average activity being Decreased, administering a medium dose of GSH as a supplement to the person;
      in response to the average activity being Low, administering a high dose of GSH as a supplement to the person;
      in response to the average activity being Normal, Increased or High, administering a low dose of GSH as a supplement to the person;
    and
  (2) evaluating activity of GGT1, and:
    in response to the activity being Increased, administering a medium dose of Q10H2 as a supplement to the person;
    in response to the activity being High, administering a high dose of Q10H2 as a supplement to the person;
    in response to the activity being Normal, Decreased or Low, administering a low dose of Q10H2 as a supplement to the person; and,
  (3) evaluating average activity of GSTM1, GSTP1, GSTT1 or GCLC, and:
    in response to the activity being Decreased, administering a medium dose of isothiocyanate as a supplement to the person;
    in response to the activity being Low, administering a high dose of isothiocyanate as a supplement to the person;

in response to the activity being Normal, Increased or High, administering a low dose of isothiocyanate as a supplement to the person; and,
(4) evaluating average activity of GPX1, GPX4 or SEPP1, and:
  in response to the activity being Decreased, administering a medium dose of selenium and alpha-lipoic acid as a supplement to the person;
  in response to the activity being Low, administering a high dose of selenium and alpha-lipoic acid as a supplement to the person;
  in response to the activity being Normal, Increased or High, or high, administering a low dose of selenium and alpha-lipoic acid as a supplement to the person; and,
  executing at least one or more of the pathway decision proprietary algorithm or the supplement intervention proprietary algorithm to evaluate average activity of SOD1 or SOD3, and:
  in response to the activity being Decreased, administering a medium dose of zinc, vitamin E and copper as supplements to the person;
  in response to the activity being Low, administering a high dose of zinc, vitamin E and copper as supplements to the person;
  in response to the activity being Normal, Increased or High, administering a low dose of zinc, vitamin E and copper as supplements to the person; and
(5) evaluating activity of SOD2, and:
  in response to the activity being Decreased, administering a medium dose of manganese and vitamin C as a supplement to the person;
  in response to the activity being Low, administering a high dose of manganese and vitamin C as a supplement to the person;
  in response to the activity being Normal, Increased or High, administering a low dose manganese and vitamin C as a supplement to the person; and
in response to the decision being to decrease GSSG level,
  evaluating GSR activity, and:
    in response to the GSR activity being Normal, administering a medium dose of B2 and/or NAD+ to the person;
    in response to the GSR activity being Increased or High, administering a low dose of B2 and/or NAD+ to the person;
    in response to the GSR activity being Decreased or Low, administering a medium dose of B2 and/or NAD+ to the person.

2. The method of claim 1, wherein:
detected levels of at least two markers in the gene-regulation pathways, metabolic pathways and signal transduction pathways are obtained from an individual sample;
and wherein the individual sample is at least one or more of saliva, blood, urine or dried blood spots.

* * * * *